US009526699B2

(12) United States Patent
Song et al.

(10) Patent No.: US 9,526,699 B2
(45) Date of Patent: Dec. 27, 2016

(54) BIODEGRADABLE AND THERMOSENSITIVE POLY(ORGANOPHOSPHAZENE) HYDROGEL, PREPARATION METHOD THEREOF AND USE THEREOF

(75) Inventors: Soo-Chang Song, Namyangju (KR); Sun-Mi Lee, Busan (KR); Chang-Won Kim, Seoul (KR); Mi-Ran Park, Seoul (KR)

(73) Assignee: KIST, Seoul (KR)

( * ) Notice: Subject to any disclaimer, the term of this patent is extended or adjusted under 35 U.S.C. 154(b) by 329 days.

(21) Appl. No.: 11/568,851

(22) PCT Filed: Nov. 3, 2006

(86) PCT No.: PCT/KR2006/004573
§ 371 (c)(1),
(2), (4) Date: Nov. 8, 2006

(87) PCT Pub. No.: WO2007/083875
PCT Pub. Date: Jul. 26, 2007

(65) Prior Publication Data
US 2009/0022683 A1    Jan. 22, 2009

(30) Foreign Application Priority Data

Jan. 18, 2006  (KR) .................. 10-2006-0005579
Apr. 4, 2006   (KR) .................. 10-2006-0030730
Nov. 1, 2006   (KR) .................. 10-2006-0107230

(51) Int. Cl.
| | | |
|---|---|---|
| A61K 38/00 | (2006.01) | |
| C08G 79/02 | (2016.01) | |
| A61K 9/00 | (2006.01) | |
| A61K 38/02 | (2006.01) | |
| A61K 39/00 | (2006.01) | |
| A61K 48/00 | (2006.01) | |
| A61K 47/30 | (2006.01) | |
| A61K 38/21 | (2006.01) | |
| A61K 38/26 | (2006.01) | |
| A61K 38/18 | (2006.01) | |
| A61K 38/20 | (2006.01) | |
| A61K 38/28 | (2006.01) | |
| A61K 38/23 | (2006.01) | |
| A61K 38/27 | (2006.01) | |
| A61K 39/395 | (2006.01) | |
| A61K 39/29 | (2006.01) | |
| A61K 31/337 | (2006.01) | |
| A61K 31/704 | (2006.01) | |
| A61K 9/06 | (2006.01) | |
| A61K 9/08 | (2006.01) | |
| A61K 47/34 | (2006.01) | |
| A61K 47/48 | (2006.01) | |

(52) U.S. Cl.
CPC ............... *A61K 9/06* (2013.01); *A61K 9/0024* (2013.01); *A61K 9/08* (2013.01); *A61K 47/34* (2013.01); *A61K 47/48784* (2013.01); *C08G 79/025* (2013.01)

(58) Field of Classification Search
CPC ........... C07K 7/06; C07K 14/001; C07K 7/64; C07K 7/08; A61K 9/0024; A61K 9/06; A61K 47/34; A61K 47/48784; A61K 9/08; C08G 79/025
See application file for complete search history.

(56) References Cited

U.S. PATENT DOCUMENTS

| | | | | |
|---|---|---|---|---|
| 4,959,442 A | * | 9/1990 | Ohkawa et al. | 528/168 |
| 4,965,397 A | | 10/1990 | Schacht et al. | |
| 5,149,543 A | * | 9/1992 | Cohen et al. | 424/499 |
| 5,464,932 A | * | 11/1995 | Allcock et al. | 528/399 |
| 5,529,777 A | * | 6/1996 | Andrianov et al. | 424/184.1 |

(Continued)

FOREIGN PATENT DOCUMENTS

| | | |
|---|---|---|
| JP | 09-500132 | 1/1997 |
| JP | 09-110996 | 4/1997 |

(Continued)

OTHER PUBLICATIONS

Gattadahalli J.C.S. Perkins 1976.*
Bae Hoon Lee, et al., Synthesis and Chracterization of Biodegradable Thermosensitive Poly(Organophosphazene) Gels, Macromoleculars, 2004, vol. 37, No. 12, pp. 4533-4537.
Bae Hoon Lee, et al., A Thermosensitive Poly(Organophosphazene) Gel, Macromoleculars, 2004, vol. 35, No. 10, pp. 3876-3879.
Kang G D et al: "Controlled release of doxorubicin from thermosensitive poly(organophosphazene) hydrogels," International Journal of Pharmaceutics 319 (2006) 29-36.

(Continued)

*Primary Examiner* — Suzanne Ziska
*Assistant Examiner* — Thurman Wheeler
(74) *Attorney, Agent, or Firm* — Lex IP Meister, PLLC

(57) ABSTRACT

The present invention relates to a biodegradable and thermosensitive poly(organophosphazene) with a functional group, a preparation method thereof, and a use thereof for delivery of bioactive substances. According to the present invention, poly(organophosphazene) is a phosphagen-based polymer showing biodegradability, thermosensitivity, and sol-gel phase transition depending on temperature change, whereby when administered into a living body with bioactive substances such as drugs, the poly(organophosphazene) forms a gel-phase at body temperature to be capable of controlled release of the bioactive substances. Further, the poly(organophosphazene) has functional groups to chemically bind with bioactive substances through an ionic bond, covalent bond, or coordinate covalent bond to be capable of a sustained release of the bioactive substances due to its good binding property. Therefore, the poly(organophosphazene) is useful as a delivery material for bioactive substances.

27 Claims, 6 Drawing Sheets

(56) References Cited

U.S. PATENT DOCUMENTS

| | | | | |
|---|---|---|---|---|
| 6,319,984 B1* | 11/2001 | Song et al. | ............... | 525/54.1 |
| 7,259,225 B2* | 8/2007 | Song et al. | ............... | 528/272 |
| 2005/0020808 A1* | 1/2005 | Song et al. | ............... | 528/492 |

FOREIGN PATENT DOCUMENTS

| | | |
|---|---|---|
| JP | 2003-514938 | 4/2003 |
| JP | 2006-089745 | 4/2006 |
| JP | 2006-117674 | 5/2006 |
| JP | 2006-525224 | 11/2006 |
| JP | 2008-530347 | 8/2008 |
| KR | 10-2001-0047025 | 6/2001 |
| KR | 10-2005-0012533 | 2/2005 |
| KR | 10-2007-46962 | 5/2007 |
| WO | 01/36516 | 5/2001 |
| WO | 03/053216 | 7/2003 |
| WO | 2005/010079 | 2/2005 |

OTHER PUBLICATIONS

Josi, R. et al. In vivo properties of an in situ forming gel for parenteral delivery of macromolecular drugs. Pharmaceutical research, 1998, vol. 15, Nr. 8, pp. 1189-1195.

Chung, Young-Me et al. Sol-gel transition temperature of PLGAgPEG aqueous solutions. Biomacromolecules, 2002, vol. 3, Nr 3, pp. 511-516.

Chang, Y. et al. Synthesis and Self-Association Behavior of Biodegradable Amphiphilic Poly [bis(ethyl glycinat-Nyl) phosphazene]—Poly (ethylene oxide) Block Copolymers. Biomacromolecules (2002), 3(6), 1364-1369.

* cited by examiner

Liquid phase
(below the initial gelling temperature)

Gel phase
(at the maximum gelling temperature)

1st week     4th week     7th week

BIODEGRADABLE AND THERMOSENSITIVE POLY(ORGANOPHOSPHAZENE) HYDROGEL, PREPARATION METHOD THEREOF AND USE THEREOF

BACKGROUND OF THE INVENTION (a) Field of the Invention

The present invention relates to a biodegradable and thermosensitive poly(organophosphazene) with a functional group, a preparation method thereof, and a use thereof for delivery of bioactive substances.

According to the present invention, poly(organophosphazene) is a phosphagen-based polymer showing biodegradability, thermosensitivity, and sol-gel phase transition depending on temperature change, whereby when administered with bioactive substances, such as drugs, into a living body, the poly(organophosphazene) forms a gel-phase at body temperature capable of controlled release of the bioactive substances. Further, the poly(organophosphazene) has functional groups to chemically bind with the bioactive substances through an ionic bond, covalent bond, or coordinate covalent bond to be capable of a sustained release of the bioactive substances due to its good binding property. Therefore, the poly(organophosphazene) is useful as a delivery material for bioactive substances.

(b) Description of the Related Art

An aqueous solution of a thermosensitive polymer hydrogel can maintain sol-phase at low temperature, and can be changed into gel-phase by raising the temperature.

Such sol-gel phase transition can occur reversibly. Thermosensitive polymer hydrogel has been considered as a useful delivery material of drugs for injection due to its advantages that the aqueous solution thereof can be easily mixed with therapeutic drugs. Therefore, it can be easily injected into a living body without any surgical operation, and when injected into a desired region of a living body, it forms a gel-phase with a three-dimensional structure at body temperature and is thereby capable of controlled and sustained release of the drugs (Nature, 388, 860 (1997), and U.S. Pat. No. 6,201,072).

However, when such thermosensitive polymer hydrogel is used as a delivery material of a drug for injection, there is a problem that drugs with small molecular weights or high hydrophilicity is that they can easily and rapidly pass through the three-dimensional network structure of the gel formed by the thermosensitive polymer hydrogel, causing a large amount of 30% or more of the drugs to be released at an early-stage of the injection. Further, there is another problem that the release of the drug is completed in a short time due to a high rate of diffusion of a hydrophilic drug from the gel into the living body, whereby a sustained release of the drug cannot be achieved (Adv Drug Deliv Rev, 31, 197 (1998)).

In order to solve such problems, various thermosensitive polymer hydrogels with a functional group capable of directly binding to drugs have been developed. When the thermosensitive polymer hydrogel is injected into a living body together with a hydrophilic drug chemically binding thereto through the functional group, the drug is released by degradation of the polymer or breakage of the chemical bond between the polymer and the drug, thereby achieving a sustained release.

It has been tried to bind N-isopropylacrylamide, which is an exemplary thermosensitive polymer, an acrylic acid copolymer that acts as a functional group, and a hydrophilic drug through a direct chemical bond. However, there is still a problem that the N-isopropylacrylamide and the acrylic acid copolymer, which bind with the drug, are cytotoxic and non-biodegradable (Macromolecules, 34, 8569, 2001).

Polyethylene oxide-polylacticglycolic acid-polyethylene oxide (PEO-PLGA-PEO, Regel) is an exemplary thermosensitive polymer hydrogel which is biodegradable in a living body. However, since the PEO-PLGA-PEO polymer has no functional group, it is not able to bind with hydrophilic drugs.

It has also been considered to chemically bind hydrophilic drugs to chitosan with a functional group to form another biodegradable and thermosensitive polymer hydrogel. However, there are still some problems in that it is difficult for chitosan to form a strong chemical bond with hydrophilic drugs due to its insolubility in an organic solvent, and it has a slow gelation rate and low gel solidity, which is undesirable for use as a delivery material of drugs.

The present inventors have reported that poly(organophosphazene)s prepared by substitution with an amino acid ester and methoxypolyethyleneglycol in a linear dichlorophosphazene molecule show a thermosensitivity that has a sol-phase in an aqueous solution at a specific temperature or lower, and a phase transition from the sol-phase to the gel-phase of a three-dimensional structure occurs with raising the temperature above the specific temperature. Further, they are gradually hydrolyzed in an aqueous solution. [Macromolecules 32, 2188 (1999); Macromolecules 32, 7820 (1999); Macromolecules 35, 3876 (2002); Korean Patent Nos. 259,367, and 315,630; and U.S. Pat. No. 6,319,984].

However, the poly(organophosphazene)s disclosed in the above documents have a limitation in being applied as a delivery material of hydrophilic drugs since they have no functional group. Therefore, in order to solve the above problems, it is required to develop novel poly(organophosphazene)s that show a sol-gel phase transition depending on a change of temperature and have a functional group capable of binding with bioactive substances.

SUMMARY OF THE INVENTION

An object of the present invention is to provide a biodegradable and thermosensitive poly(organophosphazene) with a functional group, and a method of preparation thereof.

Another object of the present invention is to provide a hydrogel containing the biodegradable and thermosensitive poly(organophosphazene) with a functional group in a specific concentration, showing the sol-gel phase transition depending on the temperature change.

Yet another object of the present invention is to provide a composition for delivery of bioactive substances containing one or more from the group consisting of the above biodegradable and thermosensitive poly(organophosphazene)s with a functional group.

Still another object of the present invention is to provide a delivery system for bioactive substances containing at least one from the group consisting of the above biodegradable and thermosensitive poly(organophosphazene)s with a functional group, and at least one bioactive substance.

DETAILED DESCRIPTION OF THE EMBODIMENTS

Figure 1:
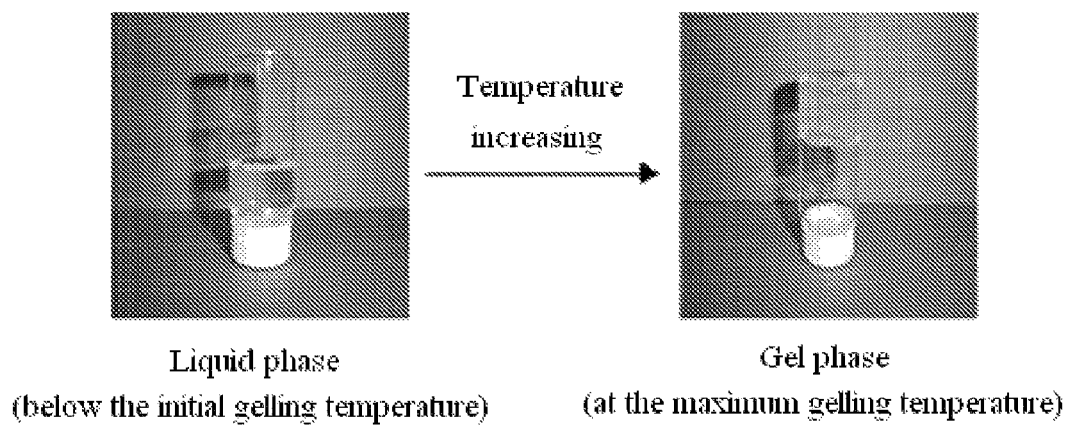
FIG. 1 is a photograph showing the sol-gel phase transition of the thermosensitive poly(organophosphazene) with a functional group of the present invention.

The present invention relates to a biodegradable and thermosensitive poly(organophosphazene) with a functional group, a preparation method thereof, and a use thereof for delivery of bioactive substances.

According to the present invention, the poly(organophosphazene) is a phosphagen-based polymer which is biodegradability and thermosensitivity, and shows sol-gel phase transition depending on temperature change. Thus, when it is administered into a living body with bioactive substances such as drugs, the poly(organophosphazene) forms a gel-phase at body temperature to allow the controlled release of the bioactive substances. Further, the poly(organophosphazene) has functional groups to chemically bond with bioactive substances through an ionic bond, covalent bond, or coordinate covalent bond to allow sustained release of the bioactive substances due to its good binding property. Therefore, the poly(organophosphazene) is useful as a delivery material for bioactive substances.

As used herein, the term 'biodegradable' refers to a property that, when a material is injected into a living body, it breaks down in vivo into harmless substances, and is excreted out, such that it does not remain in the body and has no harmful effect.

The term 'thermosensitive' refers to the property that a material shows a sol-gel phase transition in which a solution in the sol-phase is changed into the gel-phase by raising the temperature, and the temperature where the sol-gel phase transition occurs is referred to as 'gelling temperature'.

In one aspect, the present invention provides a biodegradable and thermosensitive poly(organophosphazene) with a functional group, showing a sol-gel phase transition depending on the temperature change.

The poly(organophosphazene) of the present invention may be represented by the following Chemical Formula 1:

(Chemical Formula 1)

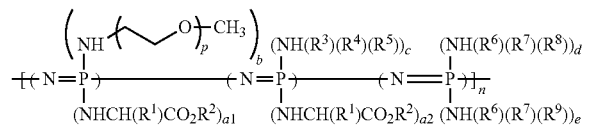

wherein, p is the number of repeating units of ethylene glycol and is an integer between 7 and 50;

$NHCH(R^1)CO_2R^2$ is an amino acid ester, wherein $R^1$ is selected from the group consisting of H, $HCH_2$, $CH_3$, $CH_2SH$, $CH(CH_3)_2$, $CH_2CH(CH_3)_2$, $CH(CH_3)C_2H_5$, $CH_2CH_2SCH_3$, $CH_2C_6H_5$, $CH_2C_6H_4OH$, $CH_2C_2NH_2C_6H_4$, $OCOC_4N^+H_9$, $CO_2C_2H_5$, $CH_2CO_2C_2H_5$, $(CH_2)_2CO_2C_2H_5$, and $HCONHCH(CH_2C_6H_5)$, and $R^2$ is selected from the group consisting of $CH_3$, $C_3H_7$, $C_4H_9$, $C_2H_5$, $CH_2C_6H_5$, and $CH_2CHCH_2$;

$NH(R^3)(R^4)(R^5)$ is an amino acid, peptide, or depsipeptide ester, wherein $R^3$ is CH(W), $R^4$ is selected from the group consisting of $CO_2$, $CO_2CH_2CO_2$, $CO_2CH(CH_3)CO_2$, and $CONHCH(X)CO_2$, $R^5$ is selected from the group consisting of H, $CH_3$, and $C_2H_5$, and W and X are independently selected from the group consisting of H, $HCH_2$, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $OCOC_4N^+H_9$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_2SH$;

$NH(R^6)(R^7)(R^8)$ and $NH(R^6)(R^7)(R^9)$ are substituents having a functional group, wherein $R^6$ is CH(Y), $R^7$ is selected from the group consisting of $C_2H_4$, $C_3H_6$, $C_4H_8$, $CH_2C_6H_4$, $CH_2CO_2$, O, CONHCH(Z)O, CO, $CO_2$, S, CONHCH(Z)S, N, CONHCH(Z)N, CON, COCHNH(Z)CON, CONHCH(Z)CO, and CONHCH(Z)$CO_2$, $R^8$ is selected from the group consisting of OH, SH, H, $CH_3$, $C_2H_5$, $C_3H_7$, $C_4H_9$, $CH_2C_6H_5$, $CH_2CHCH_2$, and protecting groups, Y and Z are independently selected from the group consisting of H, $HCH_2$, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $OCOC_4N^+H_9$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_2SH$, $R^9$ is selected from the group consisting of OH, SH, H, $NH_2$, $CH_3$, $C_2H_5$, $C_3H_7$, $C_4H_9$, $CH_2C_6H_5$, $CH_2CHCH_2$, $NHCH(SH)CO_2H$, $NH(CH_2)_qSH$, $NH(CH_2CH_2NH)_rH$, $[NHCH(C_4H_8NH_2)CO]_rOH$, $[NHCH[(CH_2)_3C(=NH)(NH_2)]CO]_rOH$, and protamines, q is the number of repeating units of methylene and is an integer between 1 and 20;

r is the number of repeating units of ethyleneimine, lysine, or arginine and is an integer between 1 and 18000;

$a_1$, $a_2$, b, c, d, and e respectively represent the content of each substituent, wherein $a_1$, $a_2$, b, and d are independently from 0.01 to 1.9, c and e are independently from 0 to 1.9, and $a_1+a_2+b+c+d+e=2.0$; and n is the degree of polymerization of the poly(organophosphazene) and is from 5 to 100000.

The protamine used as $R^9$ is not limited in the molecular weight, but preferably has a molecular weight from 4,000 to 10,000.

To give a more detail explanation for the structure of Chemical Formula 1, examples of substituents in the poly(organophosphazene)s with a functional group of the present invention are summarized in Table 1 below.

TABLE 1

| | Substituents | |
|---|---|---|
| NHCH(R¹)CO₂R² | R¹ | H, HCH₂, CH₃, CH₂SH, CH(CH₃)₂, CH₂CH(CH₃)₂, CH(CH₃)C₂H₅, CH₂CH₂SCH₃, CH₂C₆H₅, CH₂C₆H₄OH, CH₂C₂NH₂C₆H₄, OCOC₄N⁺H₉, CO₂C₂H₅, CH₂CO₂C₂H₅, (CH₂)₂CO₂C₂H₅, or HCONHCH(CH₂C₆H₅) |
| | R² | CH₃, C₂H₅, C₃H₇, C₄H₉, CH₂C₆H₅, or CH₂CHCH₂ |
| | ex. | phenylalanine ethyl ester (when R¹ = CH₂C₆H₅, R² = C₂H₅) or glycine benzyl ester (when R¹ = H, R² = CH₂C₆H₅) |
| NH(R³)(R⁴)(R⁵) | R³ | CH(W) |
| | R⁴ | CO₂, CO₂CH₂CO₂, CO₂CH(CH₃)CO₂ or CONHCH(X)CO₂ |
| | R⁵ | H, CH₃, or C₂H₅ |
| | W, X | H, HCH₂, CH₃, CH(CH₃)₂, CH₂CH(CH₃)₂, CH(CH₃)C₂H₅, CH₂CH₂SCH₃, CH₂C₆H₅, CH₂C₂NH₂C₆H₄, OCOC₄N⁺H₉, CO₂C₂H₅, (CH₂)₂CO₂C₂H₅, CH₂OH, CH(CH₃)OH, CH₂C₆H₄OH, CH₂COOH, CH₂CH₂COOH, CH₂CONH₂, C₄H₈NH₂, C₃H₆NHC(=NH)NH₂, CH₂C₃N₂H₃, or CH₂SH |
| | ex. | ethyl-2-(O-glycyl)glycolate (when R³ = CH₂, R⁴ = CO₂CH₂CO₂, and R⁵ = C₂H₅), ethyl-2-(O-glycyl)lactate (R³ = CH₂, R⁴ = CO₂CH(CH₃)CO₂, and R⁵ = C₂H₅), glycine (when R³ = CH₂, R⁴ = CO₂, and R⁵ = H), or glycylglycine (R³ = CH₂, R⁴ = CONHCH₂CO₂, and R⁵ = H) |
| NH(R⁶)(R⁷)(R⁸) and NH(R⁶)(R⁷)(R⁹) | R⁶ | CH(Y) |
| | R⁷ | C₂H₄, C₃H₆, C₄H₈, CH₂C₆H₄, CH₂CO₂, O, CONHCH(Z)O, CO, CO₂, S, CONHCH(Z)S, N, CONHCH(Z)N, CON, COCHNH(Z)CON, CONHCH(Z)CO, or CONHCH(Z)CO₂ |
| | R⁸ | OH, SH, H, CH₃, C₂H₅, C₃H₇, C₄H₉, CH₂C₆H₅, CH₂CHCH₂, or protecting groups |
| | R⁹ | OH, SH, H, NH₂, CH₃, C₂H₅, C₃H₇, C₄H₉, CH₂C₆H₅, CH₂CHCH₂, NHCH(SH)CO₂H, NH(CH₂)₄SH, NH(CH₂CH₂NH)ₙH, [NHCH(C₄H₈NH₂)CO]ₙOH, [NHCH[(CH₂)₃C(=NH)(NH₂)]CO]ₙOH, or protamines having various molecular weights |
| | Y, Z | H, HCH₂, CH₃, CH(CH₃)₂, CH₂CH(CH₃)₂, CH(CH₃)C₂H₅, CH₂CH₂SCH₃, CH₂C₆H₅, CH₂C₂NH₂C₆H₄, OCOC₄N⁺H₉, CO₂C₂H₅, (CH₂)₂CO₂C₂H₅, CH₂OH, CH(CH₃)OH, CH₂C₆H₄OH, CH₂COOH, CH₂CH₂COOH, CH₂CONH₂, C₄H₈NH₂, C₃H₆NHC(=NH)NH₂, CH₂C₃N₂H₃, or CH₂SH |
| | ex. | propyl alcohol (when R⁶ = CH₂, R⁷ = C₂H₄ and R⁸ = OH), lysine ethyl-ester (when R⁶ = CH(C₄H₈NH₂), R⁷ = CO₂, and R⁸ = C₂H₅), glycylglycine (when R⁶ = CH₂, R⁷ = CONHCH₂CO₂, and R⁸ = H), or glycyl glycyl polyethyleneimine (when R⁶ = CH₂, R⁷ = CONHCH₂CO, and R⁹ = NH(CH₂CH₂NH)ₙH) |

In one embodiment of the poly(organophosphazene) of the present invention, a hydrophobic amino acid ester and hydrophilic methoxy-polyethylene glycol having the molecular weight of 350 to 2,500 are introduced into the linear polymer of dichloro phosphazene so that the polymer can show thermosensitivity and biodegradability. Further, amino acid, peptide, and depsipeptide ester capable of controlling the degradation rate of the polymer may be partially introduced into the polymer.

In another embodiment of the present invention, the functional groups may be introduced into the poly(organophosphazene) through various methods, e.g., by directly introducing a substituent with functional groups such as hydroxyl, amide, amino, thiol, or carboxyl group on the side chain into the main chain, or introducing the amino acid ester or peptide ester substituted wherein said functional group is protected with a protecting group into the main chain of the polymer followed by removing the protecting group. The available protecting groups are summarized in the following Table 2, but not limited thereto:

TABLE 2

| Functional group | Protecting group (R' = R⁸) |
|---|---|
| Carboxyl group (RCOOR') | Fluorenylmethyl ester, Methoxymethyl ester(CH₂OCH₃), Methylthiomethyl ester(CH₂SCH₃), Tetrahydrofuranyl ester, Methoxyethoxymethyl ester(CH₂OCH₂CH₂OCH₃), 2-(trimethylsilyl)ethoxymethyl ester(CH₂OCH₂CH₂Si(CH₃)₃), Benzyloxymethyl ester(CH₂OCH₂C₆H₅), Pivaloxyloxymethyl ester(CH₂O₂CC(CH₃)₃), Phenylacetoxymethyl ester(CH₂O₂CCH₂Ph), Triisopropylsilylmethyl ester(CH₂Si-i-Pr₃), Cyanomethyl ester(CH₂CN), Acetol ester(CH₂COCH₃), Phenacyl ester(CH₂COC₆H₅), p-Bromophenacyl ester(CH₂COC₆H₄-p-Br), α-Methylphenacyl ester(CH(CH₃)COC₆H₅). p-Methoxyphenacyl ester(CH₂COC₆H₄-p-OCH₃), Desyl ester, Carboxamidomethyl ester(CH₂CONH₂), p-Azobenzenecaeboxamidomethyl ester(CH₂(O)CNHC₆H₄N=NC₆H₅), N-Phthalimidomethyl ester, 2,2,2-Trichloroethyl ester(CH₂CCl₃), 2-Haloethyl ester(CH₂CH₂X, X = I, Br, Cl), ω-Chloroalkyl ester((CH₂)ₙCl, n = 4, 5), 2-(trimethylsilyl)ethyl ester(CH₂CH₂Si(CH₃)₃), 2-Methylthioethyl ester(CH₂CH₂SCH₃), 1,3-Dithianyl-2-methyl ester, 2-(p-Nitrophenylsulfenyl)ethyl ester(CH₂CH₂SC₆H₄-p-NO₂), 2-(p-Toluenesulfonyl)ethyl ester(CH₂CH₂SO₂C₆H₄-p-CH₃), 2-(2'-Pyridyl)ethyl ester(CH₂CH₂-2-C₅H₄N), 2-(p-Methoxyphenyl)ethyl ester(CH₂CH₂C₆H₄O-p-CH₃), 2-(diphenylphosphino)ethyl ester(CH₂CH₂P(C₆H₅)₂), 1-Methyl-1-phenylethyl ester(C(CH₃)₂C₆H₅), 2-(4-Acetyl-2-nitrophenyl)ethyl ester, 2-Cyanoethyl |

TABLE 2-continued

| Functional group | Protecting group (R' = R$^8$) |
|---|---|
| | ester(CH$_2$CH$_2$CHN), t-Butyl ester(C(CH$_3$)$_3$), 3-Methyl-3-pentyl ester(CCH$_3$(C$_2$H$_4$)$_2$), Dicyclopropylmethyl ester, 2,4-Dimethyl-3-pentyl ester(CH(i-Pr)$_2$), Cyclopentyl ester(c-C$_5$H$_9$), Cyclohexyl ester(c-C$_6$H$_{11}$), Allyl ester(CH$_2$CH=CH$_2$), Methallyl ester(CH$_2$(CH$_3$)C=CH$_2$), 2-Methylbut-3-en-2-yl ester(C(CH$_3$)$_2$CH=CH$_2$), 3-Methylbut-2-enyl ester(CH$_2$CH=C(CH$_3$)$_2$), 3-Buten-1-yl ester(CH$_2$CH$_2$CH=CH$_2$), 4-(Trimethylsilyl)-2-buten-1-yl ester(CH$_2$CH=CHCH$_2$Si(CH$_3$)$_3$), Cinnamyl ester(CH$_2$CH=CHC$_6$H$_5$), α-Methylcinnamyl ester(CH(CH$_3$)CH=CHC$_6$H$_5$), Prop-2-ynyl ester(CH$_2$C≡CH), Phenyl ester(C$_6$H$_5$), 2,6-Dimethylphenyl ester, 2,6-Diisopropylphenyl ester, 2,6-Di-t-butyl-4-methylphenyl ester, 2,6-Di-t-Butyl-4-methoxyphenyl ester, p-(Methylthio)phenyl ester(C$_6$H$_4$-p-SCH$_3$), Pentafluorophenyl ester(C$_6$F$_5$), Benzyl ester(CH$_2$C$_6$H$_5$), Triphenylmethyl ester(C(C$_6$H$_5$)$_3$), Diphenylmethyl ester(CH(C$_6$H$_5$)$_2$) Bis(o-nitrophenyl)methyl ester(CH(C$_6$H$_4$-o-NO$_2$)$_2$), 9-Anthrylmethyl ester(CH$_2$-9-Anthryl), 2-(9,10-Dioxo)anthrylmethyl ester, S-dibenzosuberyl ester, 1-Pyrenylmethyl ester, 2-(trifluoromthyl)-6-chromonylmethyl ester, 2,4,6-Trimethylbenzyl ester(CH$_2$C$_6$H$_2$-2,4,6-(CH$_3$)$_3$), p-Bromobenzyl ester(CH$_2$C$_6$H$_4$-p-Br), o-Notrobenzyl ester(CH$_2$C$_6$H$_4$-o-NO$_2$), p-Nitrobenzyl ester(CH$_2$C$_6$H$_4$-p-NO$_2$), p-Methoxybenzyl ester(CH$_2$C$_6$H$_4$-p-OCH$_3$), 2,6-Dimethoxybenzyl ester(CH$_2$C$_6$H$_3$-2,6-(OCH$_3$)$_2$, 4-(Methylsulfinyl)benzyl ester(CH$_2$C$_6$H$_4$(O)S-4-CH$_3$), 4-Sulfobenzyl ester(CH$_2$C$_6$H$_4$SO$_3$$^-$Na$^+$), 4-Azidomethoxybenzyl ester(CH$_2$C$_6$H$_4$OCH$_2$N$_3$), 4-{N-[1-(4,4-Dimethyl-2,6-dioxocyclohexylidene)-3-methlbutyl]amino}benzyl ester, Piperonyl ester, 4-Picolyl ester(CH$_2$-4-pyridyl), p-P-Benzayl ester(CH$_2$C$_6$H$_4$-p-P), Trimethtylsilyl ester(Si(CH$_3$)$_3$), Triethylsilyl ester(Si(C$_2$H$_5$)$_3$), t-Butyldimethylsilyl ester(Si(CH$_3$)$_2$C(CH$_3$), i-Propyldimethylsilyl ester(Si(CH$_3$)$_2$CH(CH$_3$)$_2$), Phenyldimethylsilyl ester(Si(CH3)$_2$C$_6$H$_5$), Di-t-butylmethylsilyl ester(SiCH$_3$(t-Bu)$_2$), Triisopropylsilyl ester |
| Thiol group (RSR') | S-Alkyl thioether(C$_n$H$_{2n+1}$), S-Benzyl thioether(CH$_2$Ph), S-p-Methoxylbenzyl thioether(CH$_2$C6H4-p-OCH$_3$), S-o- or p-Hydroxy-or-Acetoxybenzyl thioether(CH$_2$C6H4-o-(or p-)-OR', R' = H or Ac), S-p-Nitrobenzyl thioether(CH$_2$C$_6$H$_4$-p-NO$_2$), S-2,4,6-Trimethylbenzyl thioether(CH$_2$C$_6$H$_2$-2,4,6-Me$_3$), S-2,4,6-Trimethoxybenzyl thioether(CH$_2$C$_6$H$_2$-2,4,6-(OMe)$_3$), S-4-Picolyl thioether(CH$_2$-4-pyridyl), S-2-Quinolinylmethyl thioether, S-2-Picolyl N-Oxide thioether(CH$_2$-2-pyridyl N-Oxide), S-9-Anthrylmethyl thioether(CH$_2$-9-anthtyl), S-9-Fluorenylmethyl thioether, S-Xanthenyl thioether, S-Ferrocenylmethyl thioether, S-Diphenylmethyl thioether(CH(C$_6$H$_5$)$_2$), S-Bis(4-methoxyphenyl)methyl thioether(CH(C$_6$H$_4$-4-OCH$_3$)$_2$), S-Bis(4-methoxyphenyl)phenylmethyl thioether, S-5-Dibenzosuberyl thioether, S-Triphenylmethyl thioether(C(C$_6$H$_5$)$_3$), S-Diphenyl-4-pyridylmethyl thioether(C(C$_6$H$_5$)$_2$-4-pyridyl), S-Phenyl thioether(C$_6$H$_5$), S-2,4-Dinitrophenyl thioether(C$_6$H$_3$-2,4-(NO$_2$)$_2$), S-t-Butyl thioether(C(CH$_3$)$_3$), S-1-Adamantyl thioether, S-Methoxymethyl monothioacetal(CH$_2$OCH$_3$), S-Isobutoxymethyl monothioacetal(CH$_2$OCH$_2$CH(CH$_3$)$_2$), S-Benzyloxymethyl monothioacetal(CH$_2$OBn), S-2-Tetrahhydropyranyl monothioacetal, S-Benzylthiomethyl dithioacetal(CH$_2$SCH$_2$C$_6$H$_5$), S-Phenylthiomethyl dithioacetal(CH$_2$SC$_6$H$_5$), 5-Acetamidometyl thioacetal(CH$_2$NHCOCH$_3$), S-Trimethylacetamidomethyl thioacetal(CH$_2$NHCOC(CH$_3$)$_3$), S-Benzamidomethyl(thioacetalCH$_2$NHCOC$_6$H$_5$), S-Allyloxycarbonylaminomethyl thioacetal(CH$_2$NH(O)COCH$_2$CH=CH$_2$), S-Phenylacetamidomethyl thioacetal(CH$_2$NH(O)CCH$_2$C$_6$H$_5$), S-Phthalimidomethyl thioacetal, S-Acetyl-, S-Carboxy, and S-Cyanomethyl thioether(CH$_2$X, X = —COCH$_3$, —CO$_2$H, —CN), S-(2-Nitro-1-phenyl)ethyl thioether(CH(C$_6$H$_5$)CH$_2$NO$_2$), S-2-(2,4-Dinitrophenyl)ethyl thioether, S-2-(4'-Pyridyl)ethyl thioether(CH$_2$CH$_2$NC$_4$H$_4$), S-2-Cyanoethyl thioether(CH$_2$CH$_2$CN), S-2-(Trimethylsilyl)ethyl thioether(CH$_2$CH$_2$TMS), S-2,2-Bis(carboethoxy)ethyl thioether(CH$_2$CH(COOC$_2$H$_5$)$_2$), S-(1-m-Nitrophenyl-2-benzoyl)ethyl thioether(CH(C$_6$H$_4$-m-NO$_2$)CH$_2$COC$_6$H$_5$), S-2-phenylsulfonylethyl thioether(CH$_2$CH$_2$SO$_2$Ph), S-1-(4-Methylphenylsulfonyl)-2-methylprop-2-yl thioether(C(CH$_3$)$_2$CH$_2$SO$_2$C$_6$H$_4$-4-CH$_3$), Triisopropylsilyl thioether, S-Acetyl derivative(COCH$_3$), S-Benzoyl derivative(COC$_6$H$_5$), S-Trifluoroacetyl derivatives(COCF$_3$), S-2,2,2-Trichloroethoxycarbonyl derivatives(COOCH$_2$CCl$_3$), S-t-Butoxycarbonyl derivatives(COOC(CH$_3$)$_3$), S-Benzyloxycarbonylderivatives(COOCH$_2$C$_6$H$_5$), S-p-Methoxybenzyloxycarbonyl derivatives(COOCH$_2$C$_6$H$_4$-p-OCH$_3$), S-(N-Ethylcarbamate)(CONHC$_2$H$_5$), S-(N-Methoxymethylcarbamate)(CONHCH$_2$OCH$_3$), S-Ethyl disulfide(SC$_2$H$_5$), S-t-Butyl disulfide(SC(CH$_3$)$_3$) |
| Hydroxy group (ROR') | Methyl ether(CH$_3$), Methoxymethyl ether(CH$_2$OCH$_3$), Methylthiomethyl ether(CH$_2$SCH$_3$), (Phenyldimethylsilyl)methoxymethyl ether(CH$_2$OCH$_2$Si(CH$_3$)$_2$C$_6$H$_5$), Benzyloxymethyl ether(CH$_2$OCH$_2$Ph), p-Methoxybenzyloxymethyl ether(CH$_2$OCH$_2$C$_6$H$_4$O-p-Me), p-Nitrobenzyloxymethyl ether(CH$_2$OCH$_2$C$_6$H$_4$-4-NO$_2$), o-Nitrobenzyloxymethyl ether(CH$_2$OCH$_2$C$_6$H$_4$-2-NO$_2$), (4-Methoxyphenoxy)methyl ether(CH$_2$OC$_6$H$_4$-4-OCH$_3$), Guaiacolmethyl ether(CH$_2$OC$_6$H$_4$-2-OMe), t-Butoxymethyl ether(CH$_2$O-t-Bu), 4-Pentenyloxymethyl ether(CH$_2$OCH$_2$CH$_2$CH$_2$CH=CH$_2$), Siloxymethyl ether(CH$_2$OSiR'R", R' = t-Bu, R" = Me; R' = Thexyl, R" = Me; R' = t-Bu, R" = Ph), 2-Methoxyethoxymethyl ether(CH$_2$OCH$_2$CH$_2$OCH$_3$), 2,2,2-Trichloroethoxymethyl ether(CH$_2$OCH$_2$CCl$_3$), Bis(2-chloroethoxy)methyl ether(CH(OCH$_2$CH$_2$Cl)$_2$), 2-(Trimethylsilyl)ethoxymethyl ether(CH$_2$OCH$_2$CH$_2$SiMe$_3$), Memthoxymethyl ether, Tetrahydropyranyl ether, 3-Bromotetrahydropyranyl ether, Tetrahydrothiopyranyl ether, 1-Methoxycyclohexyl ether, 4-Methoxytetrahydropyranyl ether, 4-Methoxytetrahydrothiopyranyl ether, 1-[(2-Chloro-4-methyl)phenyl]-4-methoxypiperidin-4-yl ether, 1-(2-Fluorophenyl)-4-methoxypiperidin-4-yl ether, 1,4-Dioxan-2-yl ether, Tetrahydrofuranyl ether, Tetrahydrothiofuranyl ether, 2,3,3a,4,5,6,7,7a-octahydro-7,8,8-trimethyl-4,7-methanobenzofuran-2-yl ether, 1-Ethoxyethyl ether(CH(OC$_2$H$_5$)CH$_3$), 1-(2-Chloroethoxy)ethyl ether(CH(CH$_3$)OCH$_2$CH$_2$Cl), 1-[2-(Trimethylsilyl)ethoxy]ethyl ether, 1-Methyl-1- |

TABLE 2-continued

| Functional group | Protecting group (R' = $R^8$) |
|---|---|
| | methoxyethyl ether(C(OCH$_3$)(CH$_3$)$_2$), 1-Methyl-1-benzyloxyethyl ether(C(OBn)(CH$_3$)$_2$), 1-Methyl-1-benzyloxy-2-fluoroethyl ether(C(OBn)(CH$_2$F)(CH$_3$), 1-Methyl-1-phenoxyethyl ether(C(OPh)(CH$_3$)$_2$), 2,2,2-trichloroethyl ether(CH$_2$CCl$_3$), 1,1-Dianisyl-2,2,2-trichloroethyl ether, 1,1,1,3,3,3-Hexafluoro-2-phenylisopropyl ether(C(CHF$_3$)$_2$Ph), 2-Trimethylsilylethyl ether(CH$_2$SiMe$_3$), 2-(Benzylthio)ethyl ether(CH$_2$CH$_2$SBn), 2-(Phenylselenyl)ethyl ether(CH$_2$CH$_2$SePh), t-Butyl ether, Allyl ether(CH$_2$CH=CH$_2$), Propargyl ether(CH$_2$C≡CH), p-Methoxyphenyl ether(C$_6$H$_4$O-p-Me), p-Nitrophenyl ether(C$_6$H$_4$-p-NO$_2$), 2,4-Dinitrophenyl ether(C$_6$H$_3$-2,4-(NO$_2$)$_2$), 2,3,5,6-Tetrafluoro-4-(trifluoromethyl)phenyl ether(C$_6$F$_4$CF$_3$), Benzyl ether(CH$_2$Ph), p-Methoxybenzyl ether(CH$_2$C$_6$H$_4$-p-OMe), 3,4-Dimethoxybenzyl ether(CH$_2$C$_6$H$_3$-3,4-(OMe)$_2$), o-Nitrobenzyl ether(CH$_2$C$_6$H$_4$-o-NO$_2$), p-Nitrobenzyl ether(CH$_2$C$_6$H$_4$-p-NO$_2$), p-Halobenzyl ether(CH$_2$C$_6$H$_4$-p-X, X = Br, Cl), 2,6-Dichlorobenzyl ether(CH$_2$C$_6$H$_3$-2,6-Cl$_2$), p-Cyanobenzyl ether(CH$_2$C$_6$H$_4$-p-CN), p-Phenylbenzyl ether(CH$_2$C$_6$H$_4$-p-C$_6$H$_5$), 2,6-Difluorobenzyl ether(CH$_2$C$_6$H$_3$F$_2$), p-Acylaminobenzyl ether(CH$_2$C$_6$H$_3$-p-NHCOR'), p-Azidobenzyl ether(CH$_2$C$_6$H$_4$-4-N$_3$), 4-Azido-3-chlorobenxyl ether(CH$_2$C$_6$H$_3$-3-Cl-4-N$_3$), 2-Trifluoromethylbenzyl ether(CH$_2$C$_6$H$_4$-2-CF$_3$), p-(Methylsulfinyl)benzyl ether(CH$_2$C$_6$H$_4$-p-(MeS(O)), 2- and 4-Picolyl ether(CH$_2$C$_5$H$_4$N), 3-Methyl-2-picolyl N-Oxido ether, 2-Quinolinylmethyl ether, 1-Pyrenylmethyl ether, Diphenylmethyl ether(CHPh$_2$), p,p'-Dinitrobenzhydryl ether(CH(C$_6$H$_4$-p-NO$_2$)$_2$), 5-Dibenzosuberyl ether, Triphenylmethyl ether, p-Methoxyphenyldiphenylmethyl ether(C(Ph)$_2$C$_6$H$_4$-p-OMe), Di(p-methoxyphenyl)phenylnethyl ether(CPh(p-MeOC$_6$H$_4$)$_2$), Tri(p-methoxyphenyl)methyl ether(C(p-MeOC$_6$H$_4$)$_3$), 4-(4'-Bromophenacyloxy)phenyldiphenylmethyl ether(C(Ph)$_2$C$_6$H$_4$-p-(OCH$_2$(O)CC$_6$H$_4$-p-Br), 4,4',4''-Tris(4,5-dichlorophthalimidophenyl)methyl ether, 4,4',4''-Tris(levulinoyloxyphenyl)methyl) ether, 4,4'4''-Tris(benzoyloxyphenyl)methyl) ether, 4,4'-Dimethoxy-3''-[N-(imidazolylmethyl)]trityl ether, 4,4'-Dimethoxy,3''-[N-(imidazolylethyl)carbamoyl)trityl ether, 1,1-Bis(4-methoxyphenyl)-1-pytenylmethyl ether, 4-(17-tetrabenzo[a,c,g,i]fluorenylmethyl)-4',4''-dimethoxytrityl ether, 9-Anthryl ether, 9-(9-Phenyl)xanthenyl ether, Tritylone ether, 1,3-Benzodithiolan-2-yl ether, Benzisothiazolyl-S,S-dioxido ether, Trimethylsilyl(Si(CH$_3$)$_3$) ether, Triethylsilyl(SiEt$_3$) ether, Triisopropylsilyl(Si(i-Pr)$_3$) ether, Dimethylisopropylsilyl(SiMe$_2$-i-Pr) ether, Diethylisopropylsilyl(SiEt$_2$-i-Pr) ether, Dimethylthesilyl ether((CH$_3$)$_2$Si(CH$_3$)$_2$CCH(CH$_3$)$_2$), t-Butyldimethylsilyl ether(SiMe$_2$-t-Bu),t-Butyldiphenylsilyl ether(SiPh$_2$-t-Bu), Tribenxylsily ether(Si(CH$_2$C$_6$H$_5$)$_3$), Tri-p-xylylsilyl ether(Si(CH$_2$C$_6$H$_4$-p-CH$_3$)$_3$), Triphenylsilyl ether(SiPh$_3$), Diphenylmethylsily ether(SiMePh$_2$), Di-t-butylmethylsilyl ether(SiMe(t-Bu)$_2$), Tris(trimethylsilyl)silyl ether([Si[Si(CH$_3$)$_3$]$_3$), (2-Hydroxystyryl)dimethylsilyl ether, (2-Hydroxystyryl)diisopropulsilyl ether, t-Butylmethoxyphenylsilyl ether(SiPh(OCH$_3$)-t-Bu), t-Butoxydiphenylsilyl ether(Si(t-OBu)Ph$_2$), Formate ester(CHO), Benzoylformate ester(COCOPh), Acetate ester(COCH$_3$), Chloroacetate ester(COCH$_2$Cl), Dichloroacetate ester(COCHCl$_2$), Trichloroacetate ester(COCCl$_3$), Trifluoroacetate ester(COCF$_3$), Methoxyacetate ester(COCH$_2$OMe), Triphenylmethoxyacetate ester(COCH$_2$OCPh$_3$), Phenoxyaetate ester(COCH$_2$OPh), p-chlorophenoxyacetate ester(COCH$_2$OC$_6$H$_4$-p-Cl), phenylacetate ester(COCH$_2$Ph), p-P-Phenylacetate ester(COCH$_2$C$_6$H$_4$-p-P), Diphenylacetate ester(COCHPh$_2$), Nicotinate ester, 3-Phenylpropionate ester(COCH$_2$CH$_2$Ph), 4-Pentenoate ester(COCH$_2$CH$_2$CH=CH$_2$), 4-Oxopentanoate ester(COCH$_2$CH$_2$COCH$_3$), 4,4-(Ethylenedithio)pentanoate ester, 5-[3-Bis(4-methoxyphenyl)hydroxymethylphenoxy]levulinic acid ester, Pivaloate(COC(CH$_3$)$_3$) ester, Crotonate ester(COCH=CHCH$_3$), 4-Methoxycrotonate ester(COCH=CHCH$_2$OCH$_3$), Benzoate ester(COPh), p-Phenylbenzoate ester(COC$_6$H$_4$-p-C$_6$H$_5$), 2,4,6-Trimethylbenzoate ester(COC$_6$H$_2$-2,4,6-Me$_3$), Alkyl methyl carbonate(CO$_2$CH$_3$), Methoxymethyl carbonate(CO$_2$CH$_2$OCH$_3$), alkyl 9-fluorenylmetyl carbonate, Alkyl ethyl carbonate(CO$_2$Et), Alkyl 2,2,2-Trichloroethyl carbonate(CO$_2$CH$_2$CCl$_3$), 1,1-Dimethyl-2,2,2-trichloroethyl carbonate(CO$_2$C(CH$_3$)$_2$CCl$_3$), Alkyl 2-(trimethylsilyl)ethyl carbonate(CO$_2$CH$_2$CH$_2$SiMe$_3$), Alkyl 2-(phenylsulfonyl)ethyl caronate(CO$_2$CH$_2$CH$_2$SO$_2$Ph), Alkyl isobutyl carbonate(CO$_2$CH$_2$CH(CH$_3$)$_2$), Alkyl vinyl carbonate(CO$_2$CH=CH$_2$), Alkyl allyl carbonate(CO$_2$CH$_2$CH=CH$_2$), Alkyl p-nitrophenyl carbonate(CO$_2$C$_6$H$_4$-p-NO$_2$), Alkyl benzyl carbonate(CO$_2$Bn), Alkyl p-methoxybenzyl carbonate(CO$_2$CH$_2$C$_6$H$_4$-p-OMe), Alkyl 3,4-dimethoxybenzyl carbonate(CO$_2$CH$_2$C$_6$H$_3$-3,4-(OMe)$_2$), Alkyl o-nitrobenzyl carbonate(CO$_2$CH$_2$C$_6$H$_4$-o-NO$_2$), Alkyl p-nitrobenzyl carbonate(CO$_2$CH$_2$C$_6$H$_4$-p-NO$_2$), 2-Dansylethyl carbonate, 2-(4-Nitrophenyl)ethyl carbonate(CO$_2$CH$_2$CH$_2$C$_6$H$_4$-4-NO$_2$), 2-(2,4-dinitrophenyl)ethyl carbonate(CO$_2$CH$_2$CH$_2$C$_6$H$_3$-2,4-(NO$_2$)$_2$), 2-Cyano-1-phenylethyl carbonate(CO$_2$(C$_6$H$_5$)CHCH$_2$CN), Alkyl S-Benzyl thiocarbonate(COSCH$_2$Ph), Alkyl 4-ethoxy-1-naphthyl carbonate, Alkyl methyl dithiocarbonate(SCSCH$_3$), 2-iodobenzoate ester(COC$_6$H$_4$-2-I), 4-Azidobutyrate ester(CO(CH$_2$)$_3$N$_3$), 4-Nitro-4-methylpentanoate ester, o-(dibromomethyl)benzoate ester(COC$_6$H$_4$-o-(CHBr$_2$)), 2-Formylbenzenesulfonate ester, Alkyl 2-(methylthiomethoxy)ethyl carbonate(CO$_2$CH$_2$CH$_2$OCH$_2$SCH$_3$), 4-(Methylthiomethoxy)butyrate ester(CO(CH$_2$)$_3$OCH$_2$SCH$_3$), 2-(Methylthiomethoxymethyl)benzoate ester(COC$_6$H$_4$-2-(CH$_2$OCH$_2$SCH$_3$)), 2-(Chloroacetoxymethyl)benzioate ester, 2-[(2-chloroacetoxy)ethyl]benzoate ester, 2-[2-(Benzyloxy)ethyl]benzoate ester, 2-[2-(4-Methoxybenzyloxy)ethyl]benzoate ester, 2,6-Dichloro-4-methylphenoxyacetate ester, 2,6-Dichloro-4-(1,1,3,3-tetramethylbutyl)phenoxyacetate ester, 2,4-Bis(1,1-dimethylpropyl)phenoxyacetate ester, Chlorodiphenylacetate ester, Isobutyrate ester, Monosuccinoate ester, (E)-2-Methyl-2-Butenoate ester, o-(Methoxycarbonyl)benzoate ester), p-P-Benzoate ester, α-Naphthoate ester, Nitrate ester, Alkyl N,N,N',N'-tetramethylphosphorodiamidate, 2-Chlorobenzoate |

TABLE 2-continued

| Functional group | Protecting group (R' = R⁸) |
|---|---|
| | ester, 4-Bromobenzoate ester, 4-Nitrobenzoate ester, 3,5-Dimethoxybenzoin carbonate, A wild and woolly photolabiled fluorescent ester, Alkyl N-phenylcarbamate, Borate ester, Dimethylphosphinothioyl ester((S)P(CH₃)₂), Alkyl 2,4-dinitrophenylsulfenate(SC₆H₃-2,4-(NO₂)₂), Sulfate, Allylsulfonate(SOCH₂CH=CH₂), Methanesulfonate (SO₂Me), Benzylsulfonate(SO₂Bn), Tosylate(SO₂C₆H₄CH₃),2-[(4-Nitrophenyl)ethyl]sulfonate(SO₂CH₂CH₂C₆H₄-4-NO₂) |
| Amino group (RNR') | Fromamide(CHO), Acetamide(Ac), Chloroacetamide(COCH₂Cl), Trichloroacetamide(COCCl₃), Trifluoroacetamide(COCF₃), Phenylacetamide(COCH₂C₆H₅), 3-Phenylpropanamide(COCH₂CH₂C₆H₅), Pent-4-enamide((O)CH₂CH₂CH=CH₂), Picolinamide(CO-2-pyridyl), 3-Pyridylcarboxamide(CO-3-Pyridyl), N-Benzoylphenylalanyl derivatives(COCH(NHCOC₆H₅)CH₂C₆H₅), Benzamide(COC₆H₅), p-Phenybenzamide(COC₆H₄-p-C₆H₅) |
| Amide group (CORNR') | N-Allylamide(CH₂CH=CH₂), N-t-Butylamide(t-Bu), N-Dicyclopropylmethylamide(CH(C₃H₅)₂), N-Methoxymethylamide(CH₂OCH₃), N-Methylthiomethylamide(CH₂SCH₃), N-Benzyloxymethylamide(CH₂OCH₂C₆H₅), N-2,2,2-Trichloroethoxymethylamide(CH₂OCH₂CCl₃), N-t-Butyldimethylsiloxymethylamide(CH₂OSi(CH3)₂-y-C₄H₉), N-Pivaloyloxymethylamide(CH₂CO₂C(CH₃)₃), N-Cyanomethylamide(CH₂CHN), N-Pyrrolidinomethylamide, N-Methoxyamide(OMe), N-Benzyloxyamide(OCH₂C₆H₅), N-Methylthioamide(SMe), N-Triphenylmethylthioamide(SCPh₃), N-t-Butyldiethylsilylamide(Si(CH₃)₂-t-C₄H₉), N-Triisopropylsilylamide(Si(i-Pr)₃), N-4-Methoxyphenylamide(C₆H₄-4-OCH₃), N-4-(Methoxymethoxy)phenylamide(C₆H₄(OCH₃)₂), N-2-Methoxy-1-naphthylamide(C₁₀H₆-2-OCH₃), N-Benzylamide(CH₂C₆H₅), N-4-Methoxybenzylamide(CH₂C₆H₄-4-OCH₃), N-2,4-Dimethoxybenzylamide N-3,4-Dimethoxybenzylamide(CH₂C₆HH₃-2,4(3,4)-(OCH₃)₂), N-2-Acetoxy-4-methoxybenzylamide(CH₂C₆HH₃-4-OMe-2-Ac), N-o-nitrobenzylamide(CH₂C₆H₄-2-NO₂), N-Bis(4-methoxyphenyl)methylamide(CH(C₆H₄-4-OMe)₂), N-Bis(4-(methoxyphenyl)phenylmethylamide(CPh-(C₆H₄-4-OMe)₂), N-Bis(4-methylsulfinylphenyl)methylamide(CH(C₆H₄(O)S-4-Me)₂), N-Triphenylmethylamide(C(C₆H₅)₃), N-9-Phenylfluorenylamide, N-t-Butoxycarbonylamide(CO-t-OC₄H₉), N-benzyloxycarbonylamide, N-Methoxycarbonylamide(COOMe), N-Ethoxycarbonylamide(COOEt), N-p-Toluenesulfonylamide, N-Butenylamide(CH=CHCH₂CH₃), N-[(E)-2-(Methoxycarbonyl)vinyl]amide(CH=CCO₂Me), N-Diethoxymethylamide(CH(OEt)₂), N-(1-Methoxy-2,2-dimethylpropyl)amide, N-2-(4-Methylphenylsulfonyl)ethylamide(CH₂CH₂SO₂C₆H₄-4-CH₃) |

In another embodiment of the present invention, lysine, arginine, cystein, thiol alkylamine, polyethyleneimines, polylysines, polyarginines, or protamines with various molecular weights may be reacted with the poly(organophosphazene) with carboxylic acid, to be introduced into the polymer as a functional group.

The gelling temperature where the sol-gel phase transition occurs, gel solidity, and/or biodegradation rate of the poly (organophosphazene) of the present invention may be controlled by the kind of hydrophobic amino acid ester, the kind of amino acid, peptide, or depsipeptide capable of controlling the degradation rate, the kind of substituent with the functional group, the chain length of methoxy polyethylene glycol, the composition of all substituents, the molecular weight of the poly(organophosphazene), the polydispersity index, the concentration of the poly(organophosphazene) solution, and the like.

For example, as the content of the hydrophobic amino acid increases, the gelling temperature becomes lower. As the concentration of the poly(organophosphazene) solution increases, the gelling temperature becomes lower and the gel solidity increases. As the chain length of methoxy polyethylene glycol increases, the gelling temperature becomes higher and the gel solidity increases. The poly(organophosphazene) with depsipeptide ester shows a higher biodegradation rate compared with a poly(organophosphazene) without depsipeptide ester. The poly(organophosphazene) with a carboxylic acid functional group shows a higher biodegradation rate compared with a poly(organophosphazene) without the carboxylic acid functional group.

In another aspect, the present invention provides a method for preparing the poly(organophosphazene) with functional groups and showing the sol-gel phase transition, represented by Chemical Formula 1. The preparation method of the present invention may include the following steps of:

(1) thermopolymerizing the phosphazene trimer (cyclotriphosphazenes) represented by the following Chemical Formula 2 to prepare a linear polymer of dichloro phosphazene represented by the following Chemical Formula 3;

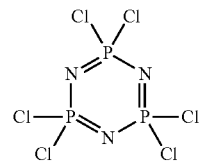

(Chemical Formula 2)

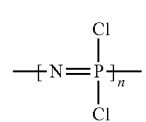

(Chemical Formula 3)

(wherein n is an integer between 7 and 100,000)

(2) reacting the compound prepared in step (1) of Chemical Formula 3 with an amino acid ester of the following Chemical Formula 4 or a salt thereof;

NH₂CH(R¹)CO₂R²            (Chemical Formula 4)

(3) reacting the compound prepared in step (2) with amino acid, peptide, depsipeptide ester, or a salt thereof, represented by the following Chemical Formula 5;

$$NH_2(R^3)(R^4)(R^5) \quad \text{(Chemical Formula 5)}$$

(4) reacting the compound prepared in step (3) with substituents having a functional group represented by the following Chemical Formula 6, or a salt thereof; and $$NH_2(R^6)(R^7)(R^8) \quad \text{(Chemical Formula 6)}$$

(5) reacting the compound prepared in step (4) with aminomethoxy polyethylene glycol represented by the following Chemical Formula 7, or a salt thereof:

$$NH_2(CH_2CH_2O)_pCH_3. \quad \text{(Chemical Formula 7)}$$

When $R^8$ is $CH_2C_6H_5$ or $CH_2CHCH_2$ in Chemical Formula 6, the preparation method of the present invention may additionally include the step (6) of dehydrogenating (when $R^8$ is $CH_2C_6H_5$), or de-allylesterifying (when $R^8$ is $CH_2CHCH_2$) the polymer prepared in step (5), to prepare the poly(organophosphazene) in which $R^8$ has a hydrogen functional group.

Moreover, the preparation method of the present invention may additionally include the step (7) of reacting the product of step (5) or (6) with lysine, arginine, cystein, thiol alkylamine, polyethyleneimines, polylysines, polyarginines, or protamines having various molecular weights, to prepare the poly(organophosphazene) in which $R^9$ has various functional groups selected from the group consisting of NHCH$(SH)CO_2H$, $NH(CH_2)_qSH$, $NH(CH_2CH_2NH)_rH$, [NH$(CH_2)_4CH(NH_2)CO]_sOH$, $[NHC(=NH)(CH_2)_3CH(NH_2)CO]_tOH$, and protamines.

The above preparation process of the poly(organophosphazene) with a functional group of Chemical Formula 1 is summarized in Reaction Formula 1:

Step (2) may be performed by reacting 1 equivalent of the product of step (1) under the presence of 0.01 to 1.9 equivalents of amino acid ester of Chemical Formula 4 or its salt and 4 equivalents of triethylamine. Preferably, said salt of the amino acid ester of Chemical Formula 4 may be sulfate or chlorohydrate. The reaction solvent may be selected from the group consisting of tetrahydrofuran, dioxane, chloroform and toluene, but is not limited thereby. The reaction may be performed at −60° C. to 50° C. for about 8 to 72 hours.

Step (3) may be performed by reacting 1 equivalent of the product of step (2) under the presence of 0 to 1.9 equivalents of amino acid, peptide, depsipeptide ester, as represented by Chemical Formula 5, or a salt thereof, and 4 equivalents of triethylamine. Preferably, said salt of the compound of Chemical Formula 5 may be oxalate, chlorohydrate, or trifluoro acid salt. The reaction solvent may be selected from the group consisting of acetonitrile, tetrahydrofuran, dioxane, chloroform, and toluene, but is not limited thereby. The reaction may be performed at 0° C. to 50° C. for about 1 to 72 hours.

Step (4) may be performed by reacting 1 equivalent of the product of step (3) under the presence of 0.01 to 1.9 equivalents of the substituent with a functional group of Chemical Formula 6 or its salt and 4 equivalents of triethylamine. Preferably, said salt of the substituent of Chemical Formula 6 may be oxalate, chlorohydrate, or trifluoro acid salt. The reaction solvent may be selected from the group consisting of acetonitrile, tetrahydrofuran, dioxane, chloroform, and toluene, but is not limited thereby. The reaction may be performed at 25° C. to 50° C. for about 12 to 72 hours.

Step (5) may be performed by reacting the product of step (4) under the presence of 2 equivalents (based on the amount (Reaction Formula 1)

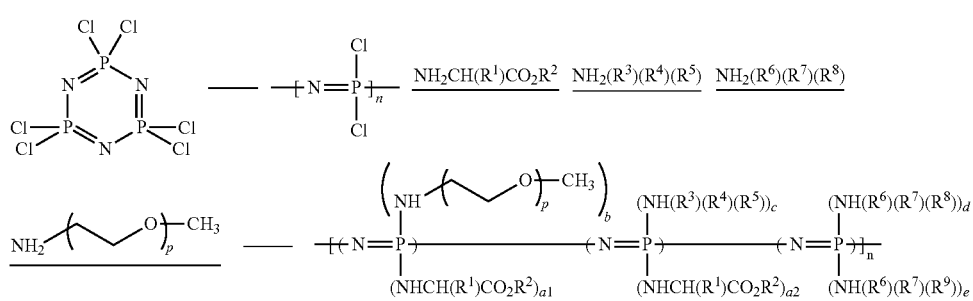

In the Chemical Formulae 4, 5, 6, and 7 and the Reaction Formula 1, $R^1$, $R^2$, $R^3$, $R^4$, $R^5$, $R^6$, $R^7$, $R^8$, $R^9$, $a_1$, $a_2$, b, c, d, e, n, and p are the same as defined for Chemical Formula 1.

Hereinafter, the preparation method of the poly(organophosphazene) with a functional group of Chemical Formula 1 will be illustrated in detail, but is not limited thereby.

All preparing reaction processes may desirably use a vacuum and/or a nitrogen line for preventing moisture being flowed in. Further, it is preferable that all solvents used in the reaction are used after sufficiently removing moisture therein by conventional methods.

Firstly, step (1) may be performed by putting the compound of Chemical Formula 2 and 0.1 to 10 wt % of AlCl$_3$ into a glass reaction tube, and after hermetically sealing the tube, reacting at 200 to 250° C. for 4 to 8 hours while stirring at 1 rpm (rotations per minute).

of remaining chlorine groups) of aminomethoxy polyethylene glycol of Chemical Formula 6 and 4 equivalents of triethylamine to substitute all the remaining chlorine groups, wherein the equivalent is calculated based on the remaining chlorine groups. The reaction solvent may be selected from the group consisting of tetrahydrofuran, dioxane, chloroform, and toluene, but is not limited thereby. The reaction may be performed at 25° C. to 50° C. for about 24 to 72 hours.

When $R^8$ is $CH_2C_6H_5$ in Chemical Formula 6, step (6) may be performed by dehydrogenating the product of step (5) under the presence of 50 to 90 wt % of palladium/charcoal or palladium black and hydrogen gas (pressure range from 30 to 80 psi), to be substituted with a carboxylic acid group. The reaction solvent may be methylalcohol or ethylalcohol, but is not limited thereby. The reaction may be performed at 10° C. to 35° C. for about 1 to 24 hours.

When $R^8$ is $CH_2CHCH_2$ in Chemical Formula 6, the step (6) may be performed by de-allylesterificating the product of step (5) under the presence of 10 to 20 mol % of tetrakis triphenylphosphin palladium (0) and 10 to 20 equivalents of morpholine, to be substituted with a carboxylic acid group. The reaction solvent may be selected from the group consisting of tetrahydrofuran, dioxane, chloroform, and toluene, but is not limited thereby. The reaction may be performed at 0° C. to 25° C. for about 1 to 24 hours.

Step (7) may be performed by reacting the product with the carboxylic acid obtained in step (5) or step (6) with one or more selected from lysine, arginine, cystein, thiol alkylamine, polyethyleneimine, polylysine, polyarginines, and protamine having various molecular weights under the presence of 1 to 3 equivalents of dicyclohexyl carbodiimide and 1 to 3 equivalents of hydroxy succinimide, to prepare the poly(organophosphazene) with various functional groups. The reaction solvent may be tetrahydrofuran or chloroform, but is not limited thereby. The reaction may be performed at 0° C. to 25° C. for about 1 to 48 hours.

In said steps (1) to (6), the product of each step may be used in the next step without purification. The pure product may be collected from the reaction mixture of steps (5), (6), and (7) through a purification process as follows:

Firstly, the reaction mixture is centrifuged or filtered to remove the precipitate (for example, triethylammonium chloride, triethylammonium salt of oxalic acid, and the like) therefrom. Then, a decompression concentration is performed until only a little solvent remains. The obtained concentrated product is dissolved in tetrahydrofuran, and an excess of ethyl ether, hexane, or a mixed solvent of ethyl ether and hexane is added thereto to induce precipitation. Then, the precipitate is filtered 2 or 3 times to remove the non-reactive substituents. The compound obtained through these processes is dissolved again in a small amount of methylalcohol or ethylalcohol. Then the reaction product is dialyzed with methylalcohol or ethylalcohol at 25° C. for 3 to 10 days, and then with distilled water at 4° C. to 25° C. for 3 to 10 days. Then the reaction product is dried under a low temperature, to obtain the pure compound as represented by Chemical Formula 1.

In another aspect, the present invention provides a polymer solution (hydrogel) containing a solution of poly(organophosphazene) of the following Chemical Formula 1-1, and showing a sol-gel phase transition depending on temperature change:

(Chemical Formula 1-1)

$$\left(\begin{array}{c}\left(NH\frown O\right)_p CH_3\end{array}\right)_b \quad (NH(R^3)(R^4)(R^5))_c \quad (NH(R^6)(R^7)(R^8))_d$$
$$\left[\left(N=P\right)\!\!-\!\!\left(N=P\right)\!\!-\!\!\left(N=P\right)\right]_n$$
$$(NHCH(R^1)CO_2R^2)_{a1} \quad (NHCH(R^1)CO_2R^2)_{a2} \quad (NH(R^6)(R^7)(R^9))_e$$

wherein p is the number of repeating units of ethylene glycol and is an integer between 7 and 50;

$NHCH(R^1)CO_2R^2$ is an amino acid ester, wherein $R^1$ is selected from the group consisting of H, $HCH_2$, $CH_3$, $CH_2SH$, $CH(CH_3)_2$, $CH_2CH(CH_3)_2$, $CH(CH_3)C_2H_5$, $CH_2CH_2SCH_3$, $CH_2C_6H_5$, $CH_2C_6H_4OH$, $CH_2C_2NH_2C_6H_4$, $OCOC_4N^+H_9$, $CO_2C_2H_5$, $CH_2CO_2C_2H_5$, $(CH_2)_2CO_2C_2H_5$, and $HCONHCH(CH_2C_6H_5)$, and $R^2$ is selected from the group consisting of $CH_3$, $C_3H_7$, $C_4H_9$, $C_2H_5$, $CH_2C_6H_5$, and $CH_2CHCH_2$;

$NH(R^3)(R^4)(R^5)$ is an amino acid, peptide or depsipeptide ester, wherein $R^3$ is CH(W), $R^4$ is selected from the group consisting of $CO_2$, $CO_2CH_2CO_2$, $CO_2CH(CH_3)CO_2$, and $CONHCH(X)CO_2$, $R^5$ is selected from the group consisting of H, $CH_3$, and $C_2H_5$, and W and X are independently selected from the group consisting of H, $HCH_2$, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $OCOC_4N^+H_9$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_2SH$;

$NH(R^6)(R^7)(R^8)$ and $NH(R^6)(R^7)(R^9)$ are substituents having a functional group, wherein $R^6$ is CH(Y), $R^7$ is selected from the group consisting of $C_2H_4$, $C_3H_6$, $C_4H_8$, $CH_2C_6H_4$, $CH_2CO_2$, O, $CONHCH(Z)O$, CO, $CO_2$, S, $CONHCH(Z)S$, N, $CONHCH(Z)N$, CON, $COCHNH(Z)$ CON, $CONHCH(Z)CO$, and $CONHCH(Z)CO_2$, $R^8$ is selected from the group consisting of OH, SH, H, $CH_3$, $C_2H_5$, $C_3H_7$, $C_4H_9$, $CH_2C_6H_5$, $CH_2CHCH_2$, and protecting groups, Y and Z are independently selected from the group consisting of H, $HCH_2$, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $OCOC_4N^+H_9$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_2SH$, $R^9$ is selected from the group consisting of OH, SH, H, $NH_2$, $CH_3$, $C_2H_5$, $C_3H_7$, $C_4H_9$, $CH_2C_6H_5$, $CH_2CHCH_2$, $NHCH(SH)CO_2H$, $NH(CH_2)_qSH$, $NH(CH_2CH_2NH)_rH$, $[NHCH(C_4H_8NH_2)CO]_rOH$, $[NHCH[(CH_2)_3C(=NH)(NH_2)]CO]_rOH$, and protamines, q is the number of repeating units of methylene and is an integer between 1 and 20, r is the number of repeating units of ethyleneimine, lysine, or arginine and is an integer between 1 and 18000;

$a_1$, $a_2$, b, c, d, and e respectively represent the content of each substituent, wherein $a_1$, $a_2$, and b are independently from 0.01 to 1.9, c, d, and e are independently from 0 to 1.9, and $a_1+a_2+b+c+d+e=2.0$; and n is the degree of polymerization of the poly(organophosphazene) and is from 5 to 100000.

The protamine used as $R^9$ is not limited in the molecular weight, but preferably has a molecular weight from 4,000 to 10,000.

As described above, the polymer solution (hydrogel) of the poly(organophosphazene) of Chemical Formula 1-1 shows a clear sol-gel phase transition depending on the temperature change, has biodegradability, and has a functional group capable of chemically binding with bioactive substances including drugs.

The hydrogel of the present invention having biodegradability and sol-gel phase transition depending on the temperature change may be a solution wherein 1 to 50 wt %, preferably from 3 to 20 wt %, of the poly(organophosphazene) of Chemical Formula 1 is dissolved in a solvent selected from the group consisting of water, buffer solution, acid solution, basic solution, salt solution, saline solution, water for injection, and glucose salt solution.

The poly(organophosphazene) of the present invention shows a sol-gel phase transition at a temperature of 5° C. to 70° C. Therefore, the poly(organophosphazene) of the present invention can be in a gel-phase under the body temperature range, and thus, can be useful as a delivery material in a body for various bioactive substances including a cell or a drug.

Furthermore, the hydrogel of the present invention has the effect of promoting the solubility of insoluble drugs. Therefore, the hydrogel of the present invention may be particularly useful in delivery of insoluble drugs including paclitaxel.

In another aspect, the present invention provides a composition for delivery of bioactive substances containing the biodegradable polymer having a gel-phase at body temperature, or a solution (hydrogel) of the above polymer, and desirable additives as described below. The polymer used in the present invention may be any polymer selected from the group consisting of the biodegradable polymers that are in a gel-phase at body temperature. The above hydrogel may be a solution wherein 1 to 50 wt %, preferably from 3 to 20 wt %, of the above polymer is dissolved in a solvent selected from the group consisting of water, buffer solution, acid solution, basic solution, salt solution, saline solution, water for injection, and glucose salt solution.

The biodegradable polymer of the present invention is characterized in that both hydrophobic and hydrophilic materials are introduced.

The polymer of the present invention optionally contains a material controlling the decomposition rate selected from the group consisting of amino acid, peptide, and depsipeptide, and/or has a functional group selected from the group consisting of hydroxyl, amide, amino, thiol, and carboxylic group on the side chain of the polymer.

The polymer of the present invention shows the sol-gel phase transition at the temperature range of 5° C. to 70° C., and may be the poly(organophosphazene) or poly(organophosphazene) hydrogel having the molecular weight of 4,000 to 400,000.

When the a composition for delivery of bioactive substances binding with the bioactive substances, such as drugs or therapeutic cells, is injected into the body, the gel-phase of a three-dimensional structure is formed at the body temperature and the bioactive substance chemically binds to the functional group, whereby, the early release of the bioactive substances in a large amount can be prevented and the release rate can be controlled to allow a sustained and effective release.

In another aspect, the present invention provides a drug delivery composition containing the poly(organophosphazene) of Chemical Formula 1-1 or the poly(organophosphazene) hydrogel:

(Chemical Formula 1-1)

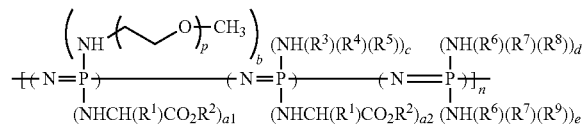

wherein p is the number of repeating units of ethylene glycol and is an integer between 7 and 50;

$NHCH(R^1)CO_2R^2$ is an amino acid ester, wherein $R^1$ is selected from the group consisting of H, $HCH_2$, $CH_3$, $CH_2SH$, $CH(CH_3)_2$, $CH_2CH(CH_3)_2$, $CH(CH_3)C_2H_5$, $CH_2CH_2SCH_3$, $CH_2C_6H_5$, $CH_2C_6H_4OH$, $CH_2C_2NH_2C_6H_4$, $OCOC_4N^+H_9$, $CO_2C_2H_5$, $CH_2CO_2C_2H_5$, $(CH_2)_2CO_2C_2H_5$, and $HCONHCH(CH_2C_6H_5)$, and $R^2$ is selected from the group consisting of $CH_3$, $C_3H_7$, $C_4H_9$, $C_2H_5$, $CH_2C_6H_5$, and $CH_2CHCH_2$;

$NH(R^3)(R^4)(R^5)$ is an amino acid, peptide, or depsipeptide ester, wherein $R^3$ is CH(W), $R^4$ is selected from the group consisting of $CO_2$, $CO_2CH_2CO_2$, $CO_2CH(CH_3)CO_2$, and $CONHCH(X)CO_2$, $R^5$ is selected from the group consisting of H, $CH_3$, and $C_2H_5$, and W and X are independently selected from the group consisting of H, $HCH_2$, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $OCOC_4N^+H_9$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_2SH$;

$NH(R^6)(R^7)(R^8)$ and $NH(R^6)(R^7)(R^9)$ are substituents having a functional group, wherein $R^6$ is CH(Y), $R^7$ is selected from the group consisting of $C_2H_4$, $C_3H_6$, $C_4H_8$, $CH_2C_6H_4$, $CH_2CO_2$, O, CONHCH(Z)O, CO, $CO_2$, S, CONHCH(Z)S, N, CONHCH(Z)N, CON, COCHNH(Z)CON, CONHCH(Z)CO, and CONHCH(Z)$CO_2$, $R^8$ is selected from the group consisting of OH, SH, H, $CH_3$, $C_2H_5$, $C_3H_7$, $C_4H_9$, $CH_2C_6H_5$, $CH_2CHCH_2$, and protecting groups, Y and Z are independently selected from the group consisting of H, $HCH_2$, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $OCOC_4N^+H_9$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_2SH$, $R^9$ is selected from the group consisting of OH, SH, H, $NH_2$, $CH_3$, $C_2H_5$, $C_3H_7$, $C_4H_9$, $CH_2C_6H_5$, $CH_2CHCH_2$, $NHCH(SH)CO_2H$, $NH(CH_2)_qSH$, $NH(CH_2CH_2NH)_rH$, $[NHCH(C_4H_8NH_2)CO]_rOH$, $[NHCH[(CH_2)_3C(=NH)(NH_2)]CO]_rOH$, and protamines, q is the number of repeating units of methylene and is an integer between 1 and 20, r is the number of repeating units of ethyleneimine, lysine, or arginine and is an integer between 1 and 18000;

$a_1$, $a_2$, b, c, d, and e respectively represent the content of each substituent, wherein $a_1$, $a_2$, and b are independently from 0.01 to 1.9, c, d, and e are independently from 0 to 1.9, and $a_1+a_2+b+c+d+e=2.0$; and n is the degree of polymerization of the poly(organophosphazene) and is from 5 to 100,000.

The protamine used as $R^9$ is not limited in molecular weight, but preferably has a molecular weight from 4,000 to 10,000.

The hydrogel showing the sol-gel phase transition depending on temperature may be a solution wherein 1 to 50 wt %, preferably from 3 to 20 wt %, of the poly(organophosphazene) of Chemical Formula 1-1 is dissolved in a solvent selected from the group consisting of water, buffer solution, acid solution, basic solution, salt solution, saline solution, water for injection, and glucose salt solution.

The drug delivery composition containing the poly(organophosphazene) of Chemical Formula 1-1 or the poly (organophosphazene) hydrogel may additionally contain the additives as described below.

In another aspect, the present invention provides a bioactive substance delivery system containing the biodegradable polymer showing the sol-gel phase transition depending on the temperature change or the polymer hydrogel, the bioactive substance, and the desired additive as described below. The polymer or the polymer hydrogel contained in the bioactive substance delivery system of the present invention is the same as described above.

In still another aspect, the present invention provides a bioactive substance delivery system containing the poly(organophosphazene) of Chemical Formula 1-1 or the poly(organophosphazene) hydrogel, and the bioactive substance:

(Chemical Formula 1-1)

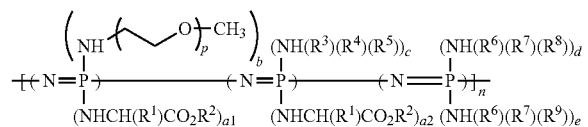

wherein p is the number of repeating units of ethylene glycol and is an integer between 7 and 50;

NHCH($R^1$)CO$_2$$R^2$ is an amino acid ester, wherein $R^1$ is selected from the group consisting of H, HCH$_2$, CH$_3$, CH$_2$SH, CH(CH$_3$)$_2$, CH$_2$CH(CH$_3$)$_2$, CH(CH$_3$)C$_2$H$_5$, CH$_2$CH$_2$SCH$_3$, CH$_2$C$_6$H$_5$, CH$_2$C$_6$H$_4$OH, CH$_2$C$_2$NH$_2$C$_6$H$_4$, OCOC$_4$N$^+$H$_9$, CO$_2$C$_2$H$_5$, CH$_2$CO$_2$C$_2$H$_5$, (CH$_2$)$_2$CO$_2$C$_2$H$_5$, and HCONHCH(CH$_2$C$_6$H$_5$), and $R^2$ is selected from the group consisting of CH$_3$, C$_3$H$_7$, C$_4$H$_9$, C$_2$H$_5$, CH$_2$C$_6$H$_5$, and CH$_2$CHCH$_2$;

NH($R^3$)($R^4$)($R^5$) is an amino acid, peptide, or depsipeptide ester, wherein $R^3$ is CH(W), $R^4$ is selected from the group consisting of CO$_2$, CO$_2$CH$_2$CO$_2$, CO$_2$CH(CH$_3$)CO$_2$, and CONHCH(X)CO$_2$, $R^5$ is selected from the group consisting of H, CH$_3$, and C$_2$H$_5$, and W and X are independently selected from the group consisting of H, HCH$_2$, CH$_3$, CH(CH$_3$)$_2$, CH$_2$CH(CH$_3$)$_2$, CH(CH$_3$)C$_2$H$_5$, CH$_2$CH$_2$SCH$_3$, CH$_2$C$_6$H$_5$, CH$_2$C$_2$NH$_2$C$_6$H$_4$, OCOC$_4$N$^+$H$_9$, CO$_2$C$_2$H$_5$, (CH$_2$)$_2$CO$_2$C$_2$H$_5$, CH$_2$OH, CH(CH$_3$)OH, CH$_2$C$_6$H$_4$OH, CH$_2$COOH, CH$_2$CH$_2$COOH, CH$_2$CONH$_2$, C$_4$H$_8$NH$_2$, C$_3$H$_6$NHC(=NH)NH$_2$, CH$_2$C$_3$N$_2$H$_3$, and CH$_2$SH;

NH($R^6$)($R^7$)($R^8$) and NH($R^6$)($R^7$)($R^9$) are substituents having a functional group, wherein $R^6$ is CH(Y), $R^7$ is selected from the group consisting of C$_2$H$_4$, C$_3$H$_6$, C$_4$H$_8$, CH$_2$C$_6$H$_4$, CH$_2$CO$_2$, O, CONHCH(Z)O, CO, CO$_2$, S, CONHCH(Z)S, N, CONHCH(Z)N, CON, COCHNH(Z)CON, CONHCH(Z)CO, and CONHCH(Z)CO$_2$, $R^8$ is selected from the group consisting of OH, SH, H, CH$_3$, C$_2$H$_5$, C$_3$H$_7$, C$_4$H$_9$, CH$_2$C$_6$H$_5$, CH$_2$CHCH$_2$, and protecting groups, Y and Z are independently selected from the group consisting of H, HCH$_2$, CH$_3$, CH(CH$_3$)$_2$, CH$_2$CH(CH$_3$)$_2$, CH(CH$_3$)C$_2$H$_5$, CH$_2$CH$_2$SCH$_3$, CH$_2$C$_6$H$_5$, CH$_2$C$_2$NH$_2$C$_6$H$_4$, OCOC$_4$N$^+$H$_9$, CO$_2$C$_2$H$_5$, (CH$_2$)$_2$CO$_2$C$_2$H$_5$, CH$_2$OH, CH(CH$_3$)OH, CH$_2$C$_6$H$_4$OH, CH$_2$COOH, CH$_2$CH$_2$COOH, CH$_2$CONH$_2$, C$_4$H$_8$NH$_2$, C$_3$H$_6$NHC(=NH)NH$_2$, CH$_2$C$_3$N$_2$H$_3$, and CH$_2$SH, $R^9$ is selected from the group consisting of OH, SH, H, NH$_2$, CH$_3$, C$_2$H$_5$, C$_3$H$_7$, C$_4$H$_9$, CH$_2$C$_6$H$_5$, CH$_2$CHCH$_2$, NHCH(SH)CO$_2$H, NH(CH$_2$)$_q$SH, NH(CH$_2$CH$_2$NH)$_r$H, [NHCH(C$_4$H$_8$NH$_2$)CO]$_r$OH, [NHCH[(CH$_2$)$_3$C(=NH)(NH$_2$)]CO]$_r$OH, and protamines, q is the number of repeating units of methylene and is an integer between 1 and 20, r is the number of repeating units of ethyleneimine, lysine, or arginine and is an integer between 1 and 18000;

$a_1$, $a_2$, b, c, d, and e respectively represent the content of each substituent, wherein $a_1$, $a_2$, and b are independently from 0.01 to 1.9, c, d, and e are independently from 0 to 1.9, and $a_1+a_2+b+c+d+e=2.0$; and n is the degree of polymerization of the poly(organophosphazene) and is from 5 to 100,000.

The protamine used as $R^9$ is not limited in the molecular weight, but preferably has a molecular weight from 4,000 to 10,000.

The hydrogel showing the sol-gel phase transition depending on temperature may be a solution wherein 1 to 50 wt %, preferably from 3 to 20 wt %, of the poly(organophosphazene) of Chemical Formula 1-1 is dissolved in a solvent selected from the group consisting of water, buffer solution, acid solution, basic solution, salt solution, saline solution, water for injection, and glucose salt solution.

The bioactive substance delivery composition containing the poly(organophosphazene) of Chemical Formula 1-1 or the poly(organophosphazene) hydrogel may additionally contain the additives as described below.

As described above, the bioactive substance delivery composition or the bioactive substance delivery system containing the polymer or the polymer hydrogel, or the bioactive substance delivery composition or the bioactive substance delivery system containing the thermosensitive poly(organophosphazene) of Chemical Formula 1-1 or the poly(organophosphazene) hydrogel may further contain various additives as described below, thereby the efficacy of the polymer hydrogel as a bioactive substance delivery material may be increased.

For example, the sol-gel phase transition of the poly(organophosphazene) solution may be controlled by addition of various salts, to achieve the desired gel solidity and gelling temperature (Macromolecules 32, 7820, 1999). When delivering a polypeptide or protein drug, the introduction of proper additives allows the stability of the drug in the hydrogel to be maintained. Further, the chemical bond including an ionic bond between additives and the drug is induced to control the release rate of the drug from the hydrogel. Moreover, when delivering therapeutic cells, the activity of the cell after delivery into the body may be increased due to the additives introduced into the hydrogel.

That is, the additives may induce various interactions for the chemical binding including an ionic bond between the poly(organophosphazene) or the poly(organophosphazene) hydrogel and the bioactive substances including drugs, to control the release of the bioactive substances, and/or increase the in vivo activity of the bioactive substances, such as, drugs or therapeutic cells.

In one embodiment of the present invention, the content of the additive is from about $1\times10^{-6}$ to 30 wt %, preferably about $1\times10^{-3}$ to 10 wt % based on the total weight of the bioactive substance delivery composition or the bioactive substance delivery system. If the content of the additive is lower than said range, the additives cannot exhibit a desired effect. On the other hand, if the content of the additive is higher than said range, the effect and/or the property of the thermosensitive polymer according to the present invention may be deteriorated.

The additive may be one or more selected from the group consisting of cationic polymers (having the molecular weight from 200 to 750,000), such as, poly-L-arginine, poly-L-lysine, poly(ethylene glycol), polyethylenimine, chitosan, protamin, and the like; anionic polymers such as poly(N-vinyl-2-pyrrolidone), polyvinylacetate (PVA), hyaluronic acid, chondroitin sulfate, heparin, alginate, and the like; bioavailable materials such as amiloride, procainamide, acetyl-beta-methylcholine, spermine, spermidine, lysozyme, fibroin, albumin, collagen, growth factors such as transforming growth factor-beta (TGF-beta), fibroblast growth factor (bFGF), vascular endothelial growth factor (VEGF), and the like, bone morphogenetic proteins (BMPs), dexamethasonfibronectin, fibrinogen, thrombin, proteins, dexrazoxane, leucovorin, ricinoleic acid, phospholipid, small intestinal submucosa, vitamin E, polyglycerol ester of fatty acid, Labrafil, Labrafil M1944CS, citric acid, glutamic acid, hydroxypropyl methylcellulose, gelatin, isopropyl myristate, Eudragit, tego betain, dimyristoylphosphatidylcholine, scleroglucan, and the like; organic solvents, such as, cremophor EL, ethanol, dimethyl sulfoxide, and the like; preservatives, such as, methylparaben and the like; sugars, such as, starch, cyclodextrin and derivatives thereof, lactose, glucose, dextran, mannose, sucrose, trehalose, maltose, ficoll, and the like; polyols, such as, innositol, mannitol, sorbitol, and the like; sugar-containing polyols, such as, sucrose-mannitol, glucose-mannitoal, and the like; amino acids, such as, alanine, arginine, glycine, and the like; polymer-containing polyols, such as, trehalose-PEG, sucrose-PEG, sucrose-dextran, and the like; sugar-containing amino acid, such as, sorbitol-glycine, sucrose-glycine, and the like; surfactants, such as, poloxamer of various molecular weights, tween 20, tween 80, triton X-100, sodium dodecyl sulfate (SDS, Brij, and the like; sugar-containing ions, such as, trehalose-$ZnSO_4$, maltose-$ZnSO_4$, and the like; and bioacceptable salts, such as, silicate, NaCl, KCl, NaBr, NaI, LiCl, n-$Bu_4NBr$, n-$Pr_4NBr$, $Et_4NBr$, $Mg(OH)_2$, $Ca(OH)_2$, $ZnCO_3$, $Ca_3(PO_4)_2$, $ZnCl_2$, $(C_2H3O_2)_2Zn$, $ZnCO_3$, $CdCl_2$, $HgCl_2$, $CoCl_2$, $(CaNO_3)_2$, $BaCl_2$, $MgCl_2$, $PbCl_2$, $AlCl_3$, $FeCl_2$, $FeCl_3$, $NiCl_2$, $AgCl$, $AuCl_3$, $CuCl_2$, sodium tetradecyl sulfate, dodecyltrimethylammonium bromide, dodecyltrmethylammonium chloride, tetradecyltrimethylammonium bromide, and the like.

The bioactive substances, which are the objectives of the composition for delivery of bioactive substances of the present invention or which are contained in the bioactive substance delivery system of the present invention, may be any substances showing any profitable effect in vivo, for example a drug or a treating cell. The drug may be selected from the group consisting of proteins, polypeptides, peptides, vaccines, genes, hormones, anti-cancer drugs, and angiogenesis inhibitors.

The proteins, polypeptides, and peptides may be selected from the group consisting of erythropoietin (EPO), interferon-alpha, interferon-beta, interferon-gamma, growth hormone (human, pig, cow, etc.), growth hormone releasing factor, nerve growth factor (NGF), granulocyte-colony stimulating factor (G-CSF), granulocyte macrophage-colony stimulating factor (GM-CSF), macrophage-colony stimulating factor (M-CSF), blood clotting factor, insulin, oxytocin, vasopressin, adrenocorticotropic hormone, epidermal growth factor, platelet-derived growth factor (PDGF), prolactin, luliberin, luteinizing hormone releasing hormone (LHRH), LHRH agonists, LHRH antagonists, somatostatin, glucagon, interleukin-2 (IL-2), interleukin-11 (IL-11), gastrin, tetragastrin, pentagastrin, urogastrone, secretin, calcitonin, enkephalins, endorphins, angiotensins, thyrotropin releasing hormone (TRH), tumor necrosis factor (TNF), tumor necrosis factor related apoptosis inducing ligand (TRAIL), heparinase, bone morphogenic protein (BMP), human atrial natriuretic peptide (hANP), glucagon-like peptide (GLP-1), renin, bradykinin, bacitracins, polymyxins, colistins, tyrocidine, gramicidins, cyclosporins and synthetic analogs thereof, monoclonal antibody, antibody, a substance which is modified or shows the same effect of a drug, ferment, and cytokines.

The vaccine may be one or more selected from the group consisting of hepatitis vaccine and the like.

The gene may be one or more selected from the group consisting of small interference RNA (siRNA), plasmid DNA, and antisense oligodeoxynucleotide (AS-ODN).

The hormone may be one or more selected from the group consisting of testosterone, estradiol, progesterone, prostaglandins and synthetic analogs thereof, and a substance which is modified or shows the same effect of a drug.

The anti-cancer drug may be one or more selected from the group consisting of paclitaxel, doxorubicin, 5-fluorouracil, cisplatin, carboplatin, oxaliplatin, tegafur, irinotecan, docetaxel, cyclophosphamide, cemcitabine, ifosfamide, mitomycin C, vincristine, etoposide, methotrexate, topotecan, tamoxifen, vinorelbine, camptothecin, danuorubicin, chlorambucil, bryostatin-1, calicheamicin, mayatansine, levamisole, DNA recombinant interferon alfa-2a, mitoxantrone, nimustine, interferon alfa-2a, doxifluridine, formestane, leuprolide acetate, megestrol acetate, carmofur, teniposide, bleomycin, carmustine, heptaplatin, exemestane, anastrozole, estramustine, capecitabine, goserelin acetate, polysaccharide potassium, medroxypogesterone acetate, epirubicin, letrozole, pirarubicin, topotecan, altretamine, toremifene citrate, BCNU, taxotere, actinomycin D, polyethylene glycol conjugated protein, and synthetic analogs thereof, and a substance which is modified or shows the same effect of a drug.

The angiogenesis inhibitor may be one or more selected from the group consisting of BMS-275291 (Bristol-Myers Squibb, New York, N.Y.), Clodronate, 6-deoxy-6-demethyl-4-dedimethylaminotetracycline (COL-3), Doxycycline, Marimastat, 2-Methoxyestradiol, Squalamine, SU5164, Thalidomide, TNP-470, Combretastatin A4, Soy Isoflavone, Enzastaurin, CC 5013 (Revimid; Celgene Corp, Warren, N.J.), Celecoxib, ZD 6474, Halofuginone hydrobromide, interferon-alpha, Bevacizumab, AE-941, Interleukin-12, VEFG-trap, Cetuximab, and synthetic analogs thereof, and a substance which is modified or shows the same effect of a drug.

The therapeutic cell may be selected from the group consisting of preosteoblast, chondrocyte, umbilical vein endothelial cell (UVEC), osteoblast, adult stem cell, schwann cell, oligodendrocyte, hepatocyte, mural cell (used in combination with UVEC), myoblast, insulin-secreting cell, endothelial cell, smooth muscle cell, fibroblast, β-cell, endodermal cell, hepatic stem cell, juxraglomerular cell, skeletal muscle cell, keratinocyte, melanocyte, langerhans cell, merkel cell, dermal fibroblast, and preadipocyte.

In the case that the bioactive substance delivery system of the present invention contains a drug as the bioactive substance, the content of the drug is from about $1 \times 10^{-8}$ to 50 vol %, preferably about $1 \times 10^{-4}$ to 20 vol % based on the total volume. If the content of the drug is lower than said range, the desired effect of the drug cannot be obtained. On the other hand, if the content of the drug is higher than said range, the property of the thermosensitive polymer can be deteriorated.

The bioactive substance delivery composition or the bioactive substance delivery system of the present invention can be in the liquid form of a sol-phase at room temperature, due to the thermosensitivity and functional group of the contained polymer. Therefore, it can be easily administered into a living body through various routes, such as, injection. Further, when the delivery composition or delivery system is injected into the body, a phase transition occurs form the sol-phase to the gel-phase by the body temperature, and thereby, the release of the bioactive substance can be easily controlled. Further, the early release of the bioactive substance in a large amount can be prevented due to the chemical bond between the bioactive substance and the functional group in the polymer of the present invention, to give a more sustained and effective release.

The bioactive substance delivery composition or the bioactive substance delivery system of the present invention can be administered to the living body through the route selected from the group consisting of oral administration, buccal administration, mucosal administration, nasal administration, intraperitoneal administration, hypodermic injection, muscular injection, percutaneous administration, and intratumoral administration, and specifically, a local administration such as hypodermic injection, muscular injection, percutaneous administration, or intratumoral administration is preferable.

The following examples will enable those skilled in the art to more clearly understand how to practice the present invention. It is to be understood that, while the invention has been described in conjunction with the preferred specific embodiments thereof, that which follows is intended to illustrate and not limit the scope of the invention. Other aspects of the invention will be apparent to those skilled in the art to which the invention pertains.

EXAMPLE

In the examples below, the elementary analysis of carbon, hydrogen, and nitrogen for the product was performed by the Property Analysis Center in the Korea Advanced Institute of Science and Technology using the Perkin-Elmer C, H, N analyzer.

The nuclear magnetic resonance spectrum with hydrogen and phosphorus is respectively measured by using Varian Gemini-300, and the average molecular weight ($M_w$) is measured through gel permeation chromatography using a Waters 1515 pump and a 2410 differentiation refractometer.

Example 1

The Preparation of poly[(phenylalanine ethyl-ester)(aminomethoxy polyethylene glycol 350)(lysine ethyl-ester)phosphazene], [NP(PheOEt)1.03(AM-PEG350)0.84(LysOEt)0.13]n Poly(dichloro phosphazene) (2.00 g, 17.26 mmol) was dissolved in tetrahydrofuran (100 ml). Phenylalanine ethyl-ester chlorohydrate (4.08 g, 17.78 mmol) and triethylamine (13.98 g, 69.04 mmol) were sequentially added thereto in a dry ice-acetone bath, and then the mixture was reacted at room temperature for 48 hours.

Tetrahydrofuran solution (50 ml) dissolving triethylamine (13.98 g, 69.04 mmol) and aminomethoxy polyethylene glycol having the molecular weight of 350 (5.44 g, 15.53 mmol) to the obtained reaction solution, to perform the reaction at the room temperature for 48 hours.

Then, the obtained reaction solution was slowly dripped into a vessel containing tetrahydrofuran solution (50 ml) in which lysine ethyl-ester chlorohydrate (1.03 g, 4.49 mmol) and triethylamine (13.98 g, 69.04 mmol) were dissolved, and reacted at room temperature for 48 hours.

The reaction solution was filtered to remove the generated triethylamine hydrochloride salt. The remaining solution after filtration was concentrated under decompression until the solvent was mostly removed. The obtained concentrate was dissolved in tetrahydrofuran (10 ml) and an excess of hexane was added thereto to form precipitation.

After the process was repeated 2 or 3 times, the obtained precipitate was again dissolved in a small amount of methylalcohol. The resulting solution was dialyzed with methylalcohol for 5 days at room temperature, and then, with distilled water for 5 days. Then, the resulting product was dried under a low temperature. 5.71 g of the end product [NP(PheOEt)$_{1.03}$(AMPEG350)$_{0.84}$(LysOEt)$_{0.13}$]$_n$ was obtained (yield 60%).

Empirical Formula: $C_{25}H_{43}N_3O_8P$
Elementary analysis data: C, 55.27; H, 7.83; N, 7.63
Theoretical value: C, 55.45; H, 7.72; N, 7.71
Hydrogen Nuclear Magnetic Resonance Spectrum (CDCl$_3$, ppm):
δ 0.8~1.2(b, —NHCH(CH$_2$C$_6$H$_5$)COOCH$_2$CH$_3$),
δ 2.9~3.2(b, —NHCH(CH$_2$C$_6$H$_5$)COOCH$_2$CH$_3$, —NHCH$_2$(CH$_2$)$_3$(NH$_2$)CHCOOCH$_2$CH$_3$),
δ 3.4(s, —NH(CH$_2$CH$_2$O)$_7$CH$_3$),
δ 3.5~3.9(b, —NH(CH$_2$CH$_2$O)$_4$CH$_3$, —NHCH(CH$_2$C$_6$H$_5$)COOCH$_2$CH$_3$),
δ 4.0~4.4(b, —NHCH(CH$_2$C$_6$H$_5$)COOCH$_2$CH$_3$),
δ 7.0~7.3(b, —NHCH(CH$_2$C$_6$H$_5$)COOCH$_2$CH$_3$)
Phosphorus Nuclear Magnetic Resonance Spectrum (CDCl$_3$, ppm): δ 17.9
Average molecular weight ($M_w$): 45,000

Example 2

The Preparation of poly[(isoleucine ethyl-ester)(aminomethoxy polyethylene glycol 550)(lysine ethyl-ester)phosphazene], [NP(IleOEt)0.86(AMPEG550)0.85(LysOEt)0.29]n The synthesis was conducted by the same method as in Example 1, except that poly(dichloro phosphazene) (2.00 g, 17.26 mmol), isoleucine ethyl-ester (1.51 g, 14.84 mmol), aminomethoxy polyethylene glycol having the molecular weight of 550 (8.07 g, 14.67 mmol), lysine ethyl-ester chlorohydrate (1.92 g, 10.01 mmol), triethylamine (15.09 g, 74.55 mmol), and tetrahydrofuran (200 ml) were used, to obtain 6.95 g of the end product [NP(IleOEt)0.86(AMPEG550)0.85(LysOEt)0.29] (yield 75%).

Empirical formula: $C_{30}H_{68}N_8O_{14}P$
Elementary analysis data: C, 47.80; H, 9.20; N, 9.60
Theoretical value: C, 48.21; H, 8.97; N, 9.58
Hydrogen Nuclear Magnetic Resonance Spectrum (CDCl$_3$, ppm):
δ 1.1~1.3(b, —NHCH(CH(CH$_3$)CH$_2$CH$_3$)OCH$_2$CH$_3$),
δ 1.3~1.6(b, —NHCH(CH(CH$_3$)CH$_2$CH$_3$)OCH$_2$CH$_3$),
δ 1.6~1.9(b, —NHCH(CH(CH$_3$)CH$_2$CH$_3$)OCH$_2$CH$_3$),
δ 2.9~3.2(b, —NHCH$_2$(CH$_2$)$_3$(NH$_2$)CHCOOCH$_2$CH$_3$),
δ 3.4(s, —NH(CH$_2$CH$_2$O)$_{11}$CH$_3$),
δ 3.5~3.9(b, —NH(CH$_2$CH$_2$O)$_{11}$CH$_3$),
δ 4.0~4.1(b, —NHCH(CH(CH$_3$)CH$_2$CH$_3$)OCH$_2$CH$_3$),
δ 4.1~4.3(b, —NHCH(CH(CH$_3$)CH$_2$CH$_3$)OCH$_2$CH$_3$)
Phosphorus Nuclear Magnetic Resonance Spectrum (CDCl$_3$, ppm): δ 18.2
Average molecular weight ($M_w$): 31,000

Example 3

The Preparation of poly[(phenylalanine ethyl-ester)(ethyl-2-(O-glycyl)lactate)(aminomethoxy polyethylene glycol 550)], [NP(IleOEt)1.10(GlyLacOEt)0.02(AMPEG550)0.88]n The synthesis was conducted by the same method as in Example 1, except that poly(dichloro phosphazene) (2.00 g, 17.26 mmol), phenylalanine ethyl-ester chlorohydrate (3.16 g, 18.99 mmol), ethyl-2-(O-glycyl)lactate ammonium oxalate (0.35 g, 0.87 mmol), aminomethoxy polyethylene glycol (molecular weight 550, 16.71 g, 30.38 mmol), triethylamine (12.06 g, 59.58 mmol) and tetrahydrofuran (200 ml) were used, to obtain 8.90 g of the end product [NP(IleOEt)$_{1.10}$(GlyLacOEt)$_{0.02}$(AMPEG550)$_{0.88}$]$_n$ (yield 74%).

Empirical formula: $C_{29}H_{70}N_5O_{14}P$

Elementary analysis data: C, 47.01; H, 9.38; N, 9.59

Theoretical value: C, 46.98; H, 8.97; N, 8.98

Hydrogen Nuclear Magnetic Resonance Spectrum (CDCl$_3$, ppm):

δ 0.8~1.2(b, —NHCH(CH(CH$_3$)CH$_2$CH$_3$)OCH$_2$CH$_3$),

δ 1.3~1.5(b, —NHCH(CH(CH$_3$)CH$_2$CH$_3$)OCH$_2$CH$_3$, —NHCH$_2$COOCH(CH$_3$)COOCH$_2$CH$_3$),

δ 1.6~1.7(b, —NHCH(CH(CH$_3$)CH$_2$CH$_3$)OCH$_2$CH$_3$, —NHCH$_2$COOCH(CH$_3$)COOCH$_2$CH$_3$,),

δ 2.9~3.2(b, —NHCH$_2$(CH$_2$)$_3$(NH$_2$)CHCOOCH$_2$CH$_3$),

δ 3.4(s, —NH(CH$_2$CH$_2$O)$_{11}$CH$_3$),

δ 3.5~3.9(b, —NH(CH$_2$CH$_2$O)$_{11}$CH$_3$),

δ 4.0~4.4(b, —NHCH$_2$COOCH(CH$_3$)COOCH$_2$CH$_3$),

δ 5.2~5.4(b, —NHCH$_2$COOCH(CH$_3$)COOCH$_2$CH$_3$,),

Phosphorus Nuclear Magnetic Resonance Spectrum (CDCl$_3$, ppm): δ 17.9

Average molecular weight (M$_w$): 392,000

Example 4

The Preparation of poly[(isoleucine ethyl-ester)(ethyl-2-(O-glycyl)glycolate)(aminomethoxy ethylene glycol 550)(lysine ethyl-ester)phosphazene], [NP(IleOEt)1.10(GlyGlycOEt)0.15(AMPEG550)0.57(LysOEt)0.16]n The synthesis was conducted by the same method as in Example 1, except that poly(dichloro phosphazene) (4.00 g, 34.50 mmol), isoleucine ethyl-ester chlorohydrate (7.43 g, 37.95 mmol), ethyl-2-(O-glycyl)glycolate ammonium oxalate (1.07 g, 5.18 mmol), aminomethoxy polyethylene glycol (molecular weight 550, 10.81 g, 19.67 mmol), lysine ethyl-ester chlorohydrate (1.36 g, 5.52 mmol), triethylamine (26.02 g, 129.39 mmol) and tetrahydrofuran (400 ml) were used, to 13.51 of the end product [NP(IleOEt)$_{1.10}$(GlyGlycOEt)$_{0.15}$(AMPEG550)$_{0.57}$(LysOEt)$_{0.16}$]$_n$ (yield 75%).

Empirical formula: $C_{25}H_{57}N_5O_{11}P$

Elementary analysis data: C, 48.12; H, 9.30; N, 11.26

Theoretical value: C, 49.41; H, 9.63; N, 10.91

The hydrogen nuclear magnetic resonance spectrum (CDCl$_3$, ppm):

δ 0.8~1.2(b, —NHCH(CH$_2$C$_6$H$_5$)COOCH$_2$CH$_3$,),

δ 1.3~1.6(b, —NHCH(CH(CH$_3$)CH$_2$CH$_3$)OCH$_2$CH$_3$, —NHCH$_2$COOCH$_2$COOCH$_2$CH$_3$,),

δ 1.6~1.9(b, —NHCH(CH(CH$_3$)CH$_2$CH$_3$)OCH$_2$CH$_3$),

δ 2.9~3.2(b, —NHCH$_2$(CH$_2$)$_3$(NH$_2$)CHCOOCH$_2$CH$_3$),

δ 3.4(s, —NH(CH$_2$CH$_2$O)$_{11}$CH$_3$),

δ 3.5~3.9(b, —NH(CH$_2$CH$_2$O)$_{11}$CH$_3$, —NHCH(CH$_2$C$_6$H$_5$)COOCH$_2$CH$_3$),

δ 4.0~4.1(b, —NHCH(CH(CH$_3$)CH$_2$CH$_3$)OCH$_2$CH$_3$, —NHCH$_2$COOCH$_2$COOCH$_2$CH$_3$,),

δ 4.1~4.3(b, —NHCH(CH(CH$_3$)CH$_2$CH$_3$)OCH$_2$CH$_3$, —NHCH$_2$COOCH$_2$COOCH$_2$CH$_3$,),

δ 5.1~5.3(b, —NHCH$_2$COOCH$_2$COOCH$_2$CH$_3$,)

The phosphorus nuclear magnetic resonance spectrum (CDCl$_3$, ppm): δ 18.1

Average molecular weight (M$_w$): 91,800

Example 5

The Preparation of poly[(isoleucine ethyl-ester)(aminomethoxy polyethylene glycol 350)(glycine)phosphazene], [NP(IleOEt)1.20(AMPEG550)0.70(GlyCOOH)0.10]n The synthesis was conducted by the same method as in Example 1, except that poly(dichloro phosphazene) (4.00 g, 34.50 mmol), isoleucine ethyl-ester (8.10 g, 44.40 mmol), aminomethoxy polyethylene glycol (molecular weight 550, 13.28 g, 24.15 mmol), glycine benzyl ester trifluoro acid salt (1.93 g, 6.90 mmol), triethylamine (31.16 g, 153.9 mmol) and tetrahydrofuran (400 ml) were used, to obtain the 16.87 g of [NP(IleOEt)$_{1.20}$(AMPEG550)$_{0.70}$(GlyOBz)$_{0.10}$]$_n$.

The obtained [NP(IleOEt)$_{1.20}$(AMPEG550)$_{0.70}$(GlyOBz)$_{0.10}$]$_n$(16.87 g) was dissolved in methylalcohol (200 ml), and the palladium/charcoal (50 wt %, 8.4 g) was added thereto. The resulting mixture was reacted under the presence of hydrogen gas of 60 to 70 psi pressure at room temperature for 12 hours. The reaction solution was filtered. The remaining solution after filtration was concentrated under decompression, and then was dissolved in a small amount of methylalcohol. The resulting solution was dialyzed with methylalcohol at room temperature for 5 days, and with distilled water at 4° C. for 5 days. Then, the resulting product was dried under a low temperature, to obtain 14.00 g of the end product [NP(IleOEt)$_{1.20}$(AMPEG550)$_{0.70}$(GlyCOOH)$_{0.10}$]$_n$ (yield 83%).

Empirical formula: $C_{26}H_{63}N_5O_{12}P$

Elementary analysis data: C, 46.95; H, 9.48; N, 10.74

Theoretical value: C, 46.21; H, 8.95; N, 10.13

The hydrogen nuclear magnetic resonance spectrum (CDCl$_3$, ppm):

δ 1.1~1.3(b, —NHCH(CH(CH$_3$)CH$_2$CH$_3$)OCH$_2$CH$_3$),

δ 1.3~1.6(b, —NHCH(CH(CH$_3$)CH$_2$CH$_3$)OCH$_2$CH$_3$),

δ 1.6~1.9(b, —NHCH(CH(CH$_3$)CH$_2$CH$_3$)OCH$_2$CH$_3$),

δ 3.3(s, —NH(CH$_2$CH$_2$O)$_{11}$CH$_3$),

δ 3.4~3.8(b, —NH(CH$_2$CH$_2$O)$_{11}$CH$_3$),

δ 3.9(s, —NHCH$_2$COOH),

δ 4.0~4.1(b, —NHCH(CH(CH$_3$)CH$_2$CH$_3$)OCH$_2$CH$_3$),

δ 4.1~4.3(b, —NHCH(CH(CH$_3$)CH$_2$CH$_3$)OCH$_2$CH$_3$)

The phosphorus nuclear magnetic resonance spectrum (CDCl$_3$, ppm): δ 19.0

Average molecular weight (M$_w$): 88,500

Example 6

The Preparation of poly[(isoleucine ethyl-ester)(aminomethoxy polyethylene glycol 350)(glycylglycine)phosphazene], [NP(IleOEt)1.23(AMPEG350)0.62(GlyGlyCOOH)0.15]n The synthesis was conducted by the same method as in Example 5, except that poly(dichloro phosphazene) (4.00 g, 34.50 mmol), isoleucine ethyl-ester (8.30 g, 42.44 mmol), aminomethoxy polyethylene glycol having the molecular weight of 350 (7.49 g, 21.39 mmol), glycylglycine benzyl ester trifluoro acid salt (3.48 g, 10.35 mmol), palladium/charcoal (8 g), triethylamine (32.07 g, 158.37 mmol), tetrahydrofuran (400 ml) and methylalcohol (200 ml) were used, to obtain 13.72 g of the end product [NP(IleOEt)$_{1.23}$(AMPEG350)$_{0.62}$(GlyGlyCOOH)$_{0.15}$]$_n$ (yield 85%).

Empirical formula: $C_{20}H_{40}N_3O_7P$

Elementary analysis data: C, 50.65; H, 8.64; N, 8.98

Theoretical value: C, 49.49; H, 8.55; N, 8.79

The hydrogen nuclear magnetic resonance spectrum (CDCl$_3$, ppm):
δ 1.1~1.3(b, —NHCH(CH(CH$_3$)CH$_2$CH$_3$)OCH$_2$CH$_3$),
δ 1.3~1.6(b, —NHCH(CH(CH$_3$)CH$_2$CH$_3$)OCH$_2$CH$_3$),
δ 1.6~1.9(b, —NHCH(CH(CH$_3$)CH$_2$CH$_3$)OCH$_2$CH$_3$),
δ 3.2(s, —NHCH$_2$CONHCH$_2$COOH),
δ 3.3(s, —NH(CH$_2$CH$_2$O)$_{11}$CH$_3$),
δ 3.4~3.8(b, —NH(CH$_2$CH$_2$O)$_{11}$CH$_3$),
δ 3.9(s, —NHCH$_2$CONHCH$_2$COOH),
δ 4.0~4.1(b, —NHCH(CH(CH$_3$)CH$_2$CH$_3$)OCH$_2$CH$_3$),
δ 4.1~4.3(b, —NHCH(CH(CH$_3$)CH$_2$CH$_3$)OCH$_2$CH$_3$)

The phosphorus nuclear magnetic resonance spectrum (CDCl$_3$, ppm): δ 19.1

Average molecular weight ($M_w$): 87,400

Example 7

The Preparation of poly[(isoleucine ethyl-ester)(aminomethoxy polyethylene glycol 550)(glycylglycine)phosphazene], [NP(IleOEt)1.23(AMPEG550)0.48(GlyGlyCOOH)0.29]n The synthesis was conducted by the same method as in Example 5, except that poly(dichloro phosphazene) (4.00 g, 34.50 mmol), isoleucine ethyl-ester (8.30 g, 42.44 mmol), aminomethoxy polyethylene glycol (molecular weight 550, 15.03 g, 27.32 mmol), glycylglycine benzyl ester trifluoro acid salt (3.48 g, 10.01 mmol), palladium/charcoal (10.5 g), triethylamine (31.86 g, 157.36 mmol), tetrahydrofuran (400 ml) and methylalcohol (200 ml) were used, to obtain 18.69 g of the end product [NP(IleOEt)$_{1.23}$(AMPEG550)$_{0.48}$(GlyGlyCOOH)$_{0.29}$]$_n$ (yield 89%).

Empirical formula: C$_{22}$H$_{44}$N$_3$O$_9$P
Elementary analysis data: C, 50.54; H, 8.50; N, 8.03
Theoretical value: C, 50.50; H, 8.23; N, 7.98

The hydrogen nuclear magnetic resonance spectrum (CDCl$_3$, ppm):
δ 1.1~1.3(b, —NHCH(CH(CH$_3$)CH$_2$CH$_3$)OCH$_2$CH$_3$),
δ 1.3~1.6(b, —NHCH(CH(CH$_3$)CH$_2$CH$_3$)OCH$_2$CH$_3$),
δ 1.6~1.9(b, —NHCH(CH(CH$_3$)CH$_2$CH$_3$)OCH$_2$CH$_3$),
δ 3.2(s, —NHCH$_2$CONHCH$_2$COOH),
δ 3.3(s, —NH(CH$_2$CH$_2$O)$_1$ CH$_3$),
δ 3.4~3.8(b, —NH(CH$_2$CH$_2$O)$_{11}$CH$_3$),
δ 3.9(s, —NHCH$_2$CONHCH$_2$COOH),
δ 4.0~4.1(b, —NHCH(CH(CH$_3$)CH$_2$CH$_3$)OCH$_2$CH$_3$),
δ 4.1~4.3(b, —NHCH(CH(CH$_3$)CH$_2$CH$_3$)OCH$_2$CH$_3$)

The phosphorus nuclear magnetic resonance spectrum (CDCl$_3$, ppm): δ 18.9

Average molecular weight ($M_w$): 108,100

Example 8

The Preparation of poly[(isoleucine ethyl-ester)(aminomethoxy polyethylene glycol 550)(glycylglycine)phosphazene], NP(IleOEt)1.17(AMPEG550)0.63(GlyGlyCOOH)0.15]n The synthesis was conducted by the same method as in Example 5, except that poly(dichloro phosphazene) (4.00 g, 34.50 mmol), isoleucine ethyl-ester (6.38 g, 40.37 mmol), aminomethoxy polyethylene glycol (molecular weight 550, 35.86 g, 65.21 mmol), glycylglycine benzyl ester trifluoro acid salt (3.48 g, 10.35 mmol), palladium/charcoal (12.5 g), triethylamine (30.81 g, 152.16 mmol) and tetrahydrofuran (400 ml) and methylalcohol (200 ml) were used, to obtain 19.08 g of the end product [NP(IleOEt)$_{1.17}$(AMPEG550)$_{0.63}$(GlyGlyCOOH)$_{0.15}$]$_n$ (yield 76%).

Empirical formula: C$_{24}$H$_{50}$N$_3$O$_{10}$P
Elementary analysis data: C, 51.25; H, 8.71; N, 7.21
Theoretical value: C, 50.98; H, 8.50; N, 7.92

The hydrogen nuclear magnetic resonance spectrum (CDCl$_3$, ppm):
δ 1.1~1.3(b, —NHCH(CH(CH$_3$)CH$_2$CH$_3$)OCH$_2$CH$_3$),
δ 1.3~1.6(b, —NHCH(CH(CH$_3$)CH$_2$CH$_3$)OCH$_2$CH$_3$),
δ 1.6~1.9(b, —NHCH(CH(CH$_3$)CH$_2$CH$_3$)OCH$_2$CH$_3$),
δ 3.2(s, —NHCH$_2$CONHCH$_2$COOH),
δ 3.3(s, —NH(CH$_2$CH$_2$O)$_7$CH$_3$),
δ 3.4~3.8(b, —NH(CH$_2$CH$_2$O)$_7$CH$_3$),
δ 3.9(s, —NHCH$_2$CONHCH$_2$COOH),
δ 4.0~4.1(b, —NHCH(CH(CH$_3$)CH$_2$CH$_3$)OCH$_2$CH$_3$),
δ 4.1~4.3(b, —NHCH(CH(CH$_3$)CH$_2$CH$_3$)OCH$_2$CH$_3$)

The phosphorus nuclear magnetic resonance spectrum (CDCl$_3$, ppm): δ 19.2

Average molecular weight ($M_w$): 98,300

Example 9

The Preparation of poly[(isoleucine ethyl-ester)(aminomethoxy polyethylene glycol 550)(glycylglycine)phosphazene], [NP(IleOEt)1.22(AMPEG550)0.66(GlyGlyCOOH)0.12]n The synthesis was conducted by the same method as in Example 5, except that poly(dichloro phosphazene) (4.00 g, 34.50 mmol), isoleucine ethyl-ester (6.65 g, 42.09 mmol), aminomethoxy polyethylene glycol (molecular weight 550, 31.31 g, 56.93 mmol), glycylglycine benzyl ester trifluoro acid salt (1.39 g, 4.14 mmol), palladium/charcoal (8.8 g), triethylamine (28.08 g, 138.69 mmol), tetrahydrofuran (400 ml) and methylalcohol 1(200 ml) were used, to obtain 15.82 g of the end product [NP(IleOEt)$_{1.22}$(AMPEG550)$_{0.66}$(GlyGlyCOOH)$_{0.12}$]$_n$ (yield 90%).

Empirical formula: C$_{25}$H$_{52}$N$_3$O$_{10}$P
Elementary analysis data: C, 51.54; H, 8.77; N, 7.10
Theoretical value: C, 51.87; H, 8.51; N, 6.89

The hydrogen nuclear magnetic resonance spectrum (CDCl$_3$, ppm):
δ 1.1~1.3(b, —NHCH(CH(CH$_3$)CH$_2$CH$_3$)OCH$_2$CH$_3$),
δ 1.3~1.6(b, —NHCH(CH(CH$_3$)CH$_2$CH$_3$)OCH$_2$CH$_3$),
δ 1.6~1.9(b, —NHCH(CH(CH$_3$)CH$_2$CH$_3$)OCH$_2$CH$_3$),
δ 3.2(s, —NHCH$_2$CONHCH$_2$COOH),
δ 3.3(s, —NH(CH$_2$CH$_2$O)$_7$CH$_3$),
δ 3.4~3.8(b, —NH(CH$_2$CH$_2$O)$_7$CH$_3$),
δ 3.9(s, —NHCH$_2$CONHCH$_2$COOH),
δ 4.0~4.1(b, —NHCH(CH(CH$_3$)CH$_2$CH$_3$)OCH$_2$CH$_3$),
δ 4.1~4.3(b, —NHCH(CH(CH$_3$)CH$_2$CH$_3$)OCH$_2$CH$_3$)

The phosphorus nuclear magnetic resonance spectrum (CDCl$_3$, ppm): δ 19.1

Average molecular weight ($M_w$): 27,200

Example 10

The Preparation of poly[(isoleucine ethyl-ester)(aminomethoxy polyethylene glycol 550)(glycylglycine)phosphazene], [NP(IleOEt)1.19(AMPEG550)0.52(GlyLeuCOOH)0.29]n The synthesis was conducted by the same method as in Example 5, except that poly(dichloro phosphazene) (4.00 g, 34.50 mmol), isoleucine ethyl-ester (8.03 g, 41.06 mmol), aminomethoxy polyethylene glycol having the molecular weight of 550 (9.87 g, 17.94 mmol), glycyl leucine benzyl ester ammonium oxalate (7.85 g, 20.01 mmol), palladium/charcoal (9.5 g), triethylamine (37.09 g, 183.21 mmol), tetrahydrofuran (400 ml) and methylalcohol (200 ml) were used, to obtain 17.11 g of the end product [NP(IleOEt)$_{1.19}$(AMPEG550)$_{0.52}$(GlyLeuCOOH)$_{0.29}$]$_n$ (yield 90%).

Empirical formula: $C_{24}H_{47}N_3O_9P$
Elementary analysis data: C, 51.65; H, 8.48; N, 7.60
Theoretical value: C, 50.91; H, 8.30; N, 7.86
The hydrogen nuclear magnetic resonance spectrum (CDCl$_3$, ppm):
δ 1.1~1.3(b, —NHCH(CH(CH$_3$)CH$_2$CH$_3$)OCH$_2$C$\underline{H}_3$, —NHCH$_2$CONHCH(CH$_2$CH(C$\underline{H}_3$)$_2$)COOH),
δ 1.3~1.6(b, —NHCH(CH(CH$_3$)C$\underline{H}_2$CH$_3$)OCH$_2$CH$_3$),
δ 1.6~1.9(b, —NHC$\underline{H}$(CH(CH$_3$)CH$_2$CH$_3$)OCH$_2$CH$_3$, —NHCH$_2$CONHCH(C$\underline{H}_2$CH(CH$_3$)$_2$)COOH),
δ 3.2(s, —NHCH$_2$CONHC$\underline{H}$(CH$_2$CH(CH$_3$)$_2$)COOH),
δ 3.3(s, —NH(CH$_2$CH$_2$O)$_{11}$C$\underline{H}_3$),
δ 3.4~3.8(b, —N(HC$\underline{H}_2$C$\underline{H}_2$O)$_{11}$CH$_3$),
δ 3.9(s, —NHCH$_2$CONHC$\underline{H}$(CH$_2$CH(CH$_3$)$_2$)COOH),
δ 4.0~4.1(b, —NHC$\underline{H}$(CH(CH$_3$)CH$_2$CH$_3$)OCH$_2$CH$_3$),
δ 4.1~4.3(b, —NHCH(CH(CH$_3$)CH$_2$CH$_3$)OC$\underline{H}_2$CH$_3$),
δ 5.1~5.3(b, —NHC$\underline{H}_2$CONHCH(CH$_2$CH(CH$_3$)$_2$)COOH).
The phosphorus nuclear magnetic resonance spectrum (CDCl$_3$, ppm): δ 20.0
Average molecular weight ($M_w$): 86,500

Example 11

The Preparation of poly[(isoleucine ethyl-ester) (aminomethoxy polyethylene glycol 550) phosphazene], [NP(IleOEt)1.19(GlyGlycOEt)0.05(AMPEG550)0.52(GlyCOOH)0.24]n The synthesis was conducted by the same method as in Example 1, except that poly(dichloro phosphazene) (4.00 g, 34.50 mmol), isoleucine ethyl-ester (8.03 g, 42.06 mmol), ethyl-2-(O-glycyl)glycolate ammonium oxalate (0.36 g, 1.73 mmol), aminomethoxy polyethylene glycol having the molecular weight of 550 (9.87 g, 17.94 mmol), glycine allylester trifluoro acetic acid salt (1.89 g, 16.56 mmol), triethylamine (36.45 g, 180.00 mmol) and tetrahydrofuran (400 ml) were used, to obtain [NP(IleOEt)$_{1.19}$(GlyGlycOEt)$_{0.05}$(AMPEG550)$_{0.52}$(GlyOAll)$_{0.24}$]$_n$ (18.6 g).

The obtained [NP(IleOEt)$_{1.19}$(GlyGlycOEt)$_{0.05}$(AMPEG550)$_{0.52}$(GlyOAll)$_{0.24}$]$_n$ (18.6 g) was dissolved in tetrahydrofuran (200 ml). The resulting solution was reacted by using the tetrakis triphenylphosphin palladium(0) (15 mol %, 1.1 g) and morpholine (20 equivalentm, 8.3 g) at room temperature for 8 hours.

The reaction solution was filtered. The remaining solution after filtration was concentrated under decompression, and was dissolved in a small amount of methylalcohol. The resulting solution was dialyzed with methylalcohol at room temperature for 5 days, and with distilled water at 4° C. for 5 days. The resulting product was dried under a low temperature, to obtain 15.81 g of the end product [NP(IleOEt)1.19(GlyGlycOEt)0.05(AMPEG550)0.52(GlyCOOH)0.24]n (yield 85%).

Empirical formula: $C_{23}H_{45}N_3O_9P$
Elementary analysis data: C, 50.63; H, 8.52; N, 7.79
Theoretical value: C, 49.47; H, 8.49; N, 7.70
The hydrogen nuclear magnetic resonance spectrum (CDCl$_3$, ppm):
δ 0.8~1.2(b, —NHCH(CH$_2$C$_6$H$_5$)COOCH$_2$C$\underline{H}_3$,),
δ 1.3~1.6(b, —NHCH(CH(CH$_3$)C$\underline{H}_2$CH$_3$)OCH$_2$CH$_3$, —NHCH$_2$COOCH$_2$COOCH$_2$C$\underline{H}_3$,),
δ 1.6~1.9(b, —NHC$\underline{H}$(CH(CH$_3$)CH$_2$CH$_3$)OCH$_2$CH$_3$),
δ 3.2(s, —NHC$\underline{H}_2$CONHCH$_2$COOH),
δ 3.3(s, —NH(CH$_2$CH$_2$O)$_{11}$C$\underline{H}_3$),
δ 3.4~3.8(b, —NH(C$\underline{H}_2$C$\underline{H}_2$O)$_{11}$CH$_3$),
δ 3.9(s, —NHCH$_2$CONHC$\underline{H}_2$COOH),
δ 4.0~4.1(b, —NHC$\underline{H}$(CH(CH$_3$)CH$_2$CH$_3$)OCH$_2$CH$_3$, —NHC$\underline{H}_2$COOCH$_2$COOCH$_2$CH$_3$,),
δ 4.1~4.3(b, —NHCH(CH(CH$_3$)CH$_2$CH$_3$)OC$\underline{H}_2$CH$_3$, —NHCH$_2$COOCH$_2$COOC$\underline{H}_2$CH$_3$,),
δ 5.1~5.3(b, —NHCH$_2$COOC$\underline{H}_2$COOCH$_2$CH$_3$,),
The phosphorus nuclear magnetic resonance spectrum (CDCl$_3$, ppm): δ 19.1
Average molecular weight ($M_w$): 87,400

Example 12

The Preparation of poly[(isoleucine ethyl-ester) (ethyl-2-(O-glycyl)lactate)(aminomethoxy polyethylene glycol 750)(glycylglycine)phosphazene], [NP(IleOEt)1.27(GlyLacOEt)0.15(AMPEG750)0.45(GlyGlyCOOH)0.13]n The synthesis was conducted by the same method as in Example 11, except that poly(dichloro phosphazene) (4.00 g, 34.50 mmol), isoleucine ethyl-ester (8.57 g, 43.82 mmol), ethyl-2-(O-glycyl) lactate ammonium oxalate (1.13 g, 5.18 mmol), aminomethoxy polyethylene glycol (molecular weight 750, 11.64 g, 15.53 mmol), glycylglycine allylester trifluoro acetic acid salt (2.57 g, 8.97 mmol), tetrakis triphenylphosphin palladium(0) (1.12 g), morpholine (8.45 g), triethylamine (29.77 g, 147.00 mmol) and tetrahydrofuran (600 ml) were used, to obtain 19.61 g of the end product [NP(IleOEt)$_{1.27}$(GlyLacOEt)$_{0.15}$(AMPEG750)$_{0.45}$(GlyGlyCOOH)$_{0.13}$]$_n$ (yield 95%).

Empirical formula: $C_{26}H_{52}N_3O_{101}P$
Elementary analysis data: C, 51.50; H, 8.64; N, 7.02
Theoretical value: C, 50.98; H, 8.46; N, 7.07
The hydrogen nuclear magnetic resonance spectrum (CDCl$_3$, ppm):
δ 1.1~1.3(b, —NHCH(CH(CH$_3$)CH$_2$CH$_3$)OCH$_7$C$\underline{H}_3$),
δ 1.3~1.6(b, —NHCH(CH(CH$_3$)C$\underline{H}_2$CH$_3$)OCH$_2$CH$_3$, —NHCH$_2$COOCH(CH$_3$)COOCH$_2$C$\underline{H}_3$),
δ 1.6~1.9(b, —NHC$\underline{H}$(CH(CH$_3$)CH$_2$CH$_3$)OCH$_2$CH$_3$, —NHCH$_2$COOCH(C$\underline{H}_3$)COOCH$_2$CH$_3$),
δ 3.2(s, —NHC$\underline{H}_2$CONHCH$_2$COOH),
δ 3.3(s, —NH(CH$_2$CH$_2$O)$_{15}$C$\underline{H}_3$),
δ 3.4~3.8(b, —NH(C$\underline{H}_2$C$\underline{H}_2$O)$_{15}$CH$_3$),
δ 3.9(s, —NHCH$_2$CONHC$\underline{H}_2$COOH),
δ 4.0~4.1(b, —NHC$\underline{H}$(CH(CH$_3$)CH$_2$CH$_3$)OCH$_2$CH$_3$),
δ 4.1~4.4(b, —NHCH(CH(CH$_3$)CH$_2$CH$_3$)OC$\underline{H}_2$CH$_3$, —NHC$\underline{H}_2$COOCH(CH$_3$)COOC$\underline{H}_2$CH$_3$),
δ 5.2~5.4(b, —NHCH$_2$COOC$\underline{H}$(CH$_3$)COOCH$_2$CH$_3$,)
The phosphorus nuclear magnetic resonance spectrum (CDCl$_3$, ppm): δ 19.3
Average molecular weight ($M_w$): 49,600

Example 13

The Preparation of poly[(isoleucine ethyl-ester) (aminomethoxy polyethylene glycol 550)(glycylglycine)(glycyl glycyl polyethyleneimine)phosphazene], [NP(IleOEt)1.19(AMPEG550)0.62(GlyGlyCOOH)0.04(GlyGlyPEI800)0.15]n The synthesis was conducted by the same method as in Example 11, except that poly(dichloro phosphazene) (4.00 g, 34.50 mmol), isoleucine ethyl-ester (8.15 g, 41.06 mmol), aminomethoxy polyethylene glycol (molecular weight 550, 11.76 g, 21.39 mmol), glycylglycine allylester trifluoro acetic acid salt (1.88 g, 6.65 mmol), tetrakis triphenylphosphin palladium(0) (1.68 g), morpholine (12.68 g), triethylamine (28.98 g, 143.13 mmol) and tetrahydrofuran (600 ml) were used, to obtain $[NP(IleOEt)_{1.19}(AMPEG550)_{0.62}(GlyGlyCOOH)_{0.19}]_n$ (20.05 g).

The obtained $[NP(IleOEt)_{1.19}(AMPEG550)_{0.62}(GlyGlyCOOH)_{0.19}]_n$ (20.05 g) was dissolved in tetrahydrofuran (200 ml). The resulting solution was reacted by using poly(ethylene imine) (0.15 equivalent, molecular weight 800, 10.59 g), dicyclohexyl carbodiimide (0.24 equivalent, 1.36 g) and hydroxyl succinimide (0.24 equivalent, 0.762 g) at room temperature for 48 hours.

The reaction solution was filtered. The remaining solution after filtration was concentrated under decompression, and was dissolved in a small amount of methylalcohol. The resulting solution was dialyzed with methylalcohol at room temperature for 5 days, and with distilled water at 4° C. for 5 days. The resulting product was dried under a low temperature, to obtain 17.64 g of the end product [NP(IleOEt)1.19(AMPEG550)0.62(GlyGlyCOOH)0.04(GlyGlyPEI800)0.15]n (yield 88%).

Empirical formula: $C_{30}H_{59}N_5O_{11}P$

Elementary analysis data: C, 51.39; H, 8.42; N, 9.91

Theoretical value: C, 41.89; H, 8.70; N, 10.64

The hydrogen nuclear magnetic resonance spectrum (CDCl$_3$, ppm):

δ 1.1~1.3(b, —NHCH(CH(CH$_3$)CH$_2$CH$_3$)OCH$_2$C$\underline{H}_3$),

δ 1.3~1.6(b, —NHCH(CH(CH$_3$)C$\underline{H}_2$CH$_3$)OCH$_2$CH$_3$),

δ 1.6~1.9(b, —NHCH(C$\underline{H}$(CH$_3$)CH$_2$CH$_3$)OCH$_2$CH$_3$),

δ 2.1~2.6(b, —NH(C$\underline{H_2CH_2}$NH)$_{18}$H),

δ 3.2(s, —NHC$\underline{H}_2$CONHCH$_2$COOH),

δ 3.3(s, —NH(CH$_2$CH$_2$O)$_{11}$C$\underline{H}_3$),

δ 3.4~3.8(b, —NH(C$\underline{H_2CH_2}$O)$_{11}$CH$_3$),

δ 3.9(s, —NHCH$_2$CONHC$\underline{H}_2$COOH),

δ 4.0~4.1(b, —NHC$\underline{H}$(CH(CH$_3$)CH$_2$CH$_3$)OCH$_2$CH$_3$),

δ 4.1~4.4(b, —NHCH(CH(CH$_3$)CH$_2$CH$_3$)OC$\underline{H}_2$CH$_3$).

The phosphorus nuclear magnetic resonance spectrum (CDCl$_3$, ppm): δ 19.5

Average molecular weight ($M_w$): 52,700

Example 14

Observation of the Sol-Gel Phase Transition of poly(organophosphazene) Polymers Depending on the Temperature The poly(organophosphazene)s obtained in Examples 1 to 13 were respectively dissolved in phosphate buffered saline (pH 7.4) at 4° C. to make solutions with concentrations of 10 wt %. The solutions were put into a chamber of a Brookfield DV-III+ Rheometer equipped with a thermostatic bath (TC-501). The sol-gel phase transition was observed with raising the temperature at the rate of 0.04° C./min and the shear rate of 0.1 to 1.7 per second.

FIG. 1 is a photograph showing the sol-gel phase transition of the poly(organophosphazene) of the present invention with the temperature change. It shows that at a temperature below the initial gelling temperature, the polymer solution is in the fluid sol-phase, and at the maximum gelling temperature above the initial gelling temperature, it changed into the gel-phase.

The gel properties of the thermosensitive poly(organophosphazene)s of the present invention depending on the temperature observed as above are shown in the following Table 3:

TABLE 3

| Polymer | Structure | Max. gelling temp. (° C.) | Max. gel solidity (Pa · s) |
|---|---|---|---|
| Example 1 | [NP(PheOEt)$_{1.03}$(AMPEG350)$_{0.84}$(LysOEt)$_{0.13}$]$_n$ | 1 | 6 |
| Example 2 | [NP(IleOEt)$_{0.86}$(AMPEG550)$_{0.85}$(LysOEt)$_{0.29}$]$_n$ | 7 | 50 |
| Example 3 | [NP(IleOEt)$_{1.10}$(GlyLacOEt)$_{0.02}$(AMPEG550)$_{0.88}$]$_n$ | 2 | 15 |
| Example 4 | [NP(IleOEt)$_{1.10}$(GlyGlycOEt)$_{0.15}$(AMPEG550)$_{0.57}$(LysOEt)$_{0.16}$]$_n$ | 9 | 28 |
| Example 5 | [NP(IleOEt)$_{1.20}$(AMPEG550)$_{0.70}$(GlyCOOH)$_{0.10}$]$_n$ | 7 | 53 |
| Example 6 | [NP(IleOEt)$_{1.23}$(AMPEG350)$_{0.62}$(GlyGlyCOOH)$_{0.15}$]$_n$ | 8 | 00 |
| Example 7 | [NP(IleOEt)$_{1.23}$(AMPEG550)$_{0.48}$(GlyGlyCOOH)$_{0.29}$]$_n$ | 7 | 058 |
| Example 8 | [NP(IleOEt)$_{1.23}$(AMPEG550)$_{0.62}$(GlyGlyCOOH)$_{0.15}$]$_n$ | 1 | 5 |
| Example 9 | [NP(IleOEt)$_{1.22}$(AMPEG550)$_{0.66}$(GlyGlyCOOH)$_{0.12}$]$_n$ | 9 | 8 |
| Example 10 | [NP(IleOEt)$_{1.17}$(AMPEG550)$_{0.63}$(GlyLeuCOOH)$_{0.15}$]$_n$ | 6 | 82 |
| Example 11 | [NP(IleOEt)$_{1.19}$(GlyGlycOEt)$_{0.05}$(AMPEG550)$_{0.52}$(GlyCOOH)$_{0.24}$]$_n$ | 8 | 15 |
| Example 12 | [NP(IleOEt)$_{1.27}$(GlyLacOEt)$_{0.15}$(AMPEG750)$_{0.45}$(GlyGlyCOOH)$_{0.13}$]$_n$ | 1 | 8 |
| Example 13 | [NP(IleOEt)$_{1.19}$(AMPEG550)$_{0.62}$(GlyGlyCOOH)$_{0.04}$(GlyGlyPEI800)$_{0.15}$]$_n$ | 9 | 57 |

In Table 3, the term 'max. (maximum) gelling temp. (temperature)' means the temperature where the viscosity of the polymer solution reaches the maximum point, and the term 'max. gel solidity' means the maximum viscosity of the polymer solution.

Figure 2:
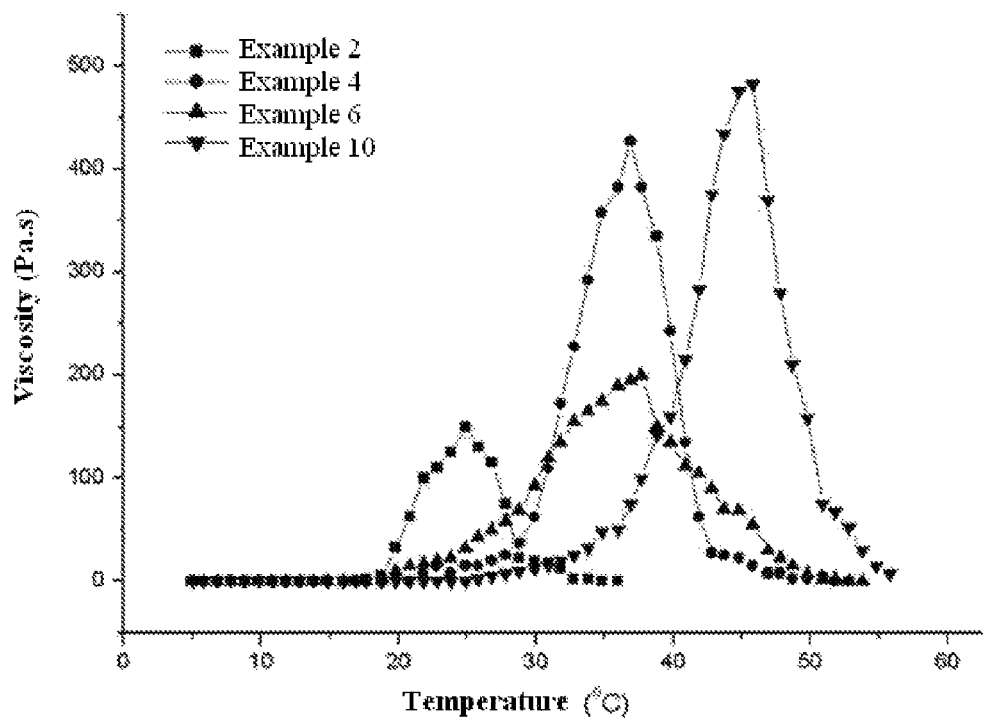
FIG. 2 shows the changes in the viscosity of the poly(organophosphazene) with a functional group of the present invention depending on the temperature change.

The changes of the viscosity of the poly(organophosphazene)s of the present invention depending on the temperature are shown in FIG. 2.

As known from Table 3 and FIG. 2, the poly(organophosphazene)s with a wide range of the maximum gelling temperature and the maximum gel solidity can be confirmed by regulating the kind of the hydrophobic amino acid ester substituted in the polymer, the kind of amino acid, peptide, or depsipeptide capable of controlling the degradation rate, the kind of amino acid or peptide with a functional group, the chain length of methoxypolyethyleneglycol, and the composition of all the substituents.

Example 15

Observation of the Degree of Hydrolysis of the poly(organophosphazene) with Time The poly(organophosphazene)s obtained in the examples of the present invention were respectively dissolved in phosphate buffered saline (pH 7.4) to make solutions with a concentration of 10 wt %, and then, the solutions were kept in a bath at 37° C. The degree of hydrolysis of the polymer with time was determined in terms of the degree of the reduced molecular weight of the polymer measured by Gel Permeation Chromatography (GPC) depending on lapse of time. The obtained results are shown in the following Table 4.

Deleted Texts

According to analysis of the components of the polymer solution decomposed for a certain time, phosphates, ammonia, ethylalcohol, and the like, were depected from the polymer solution. Therefore, it can be presumed that the poly(organophosphazene)s with a functional group should be decomposed into ingredients harmless to a living body, such as phosphates, ammonia, ethylalcohol, and the like.

TABLE 4

| | Change of the Molecular Weight of the Polymer (%) | | | | | | |
|---|---|---|---|---|---|---|---|
| Polymer | Day 0 | Day 1 | Day 3 | Day 5 | Day 6 | Day 10 | Day 14 | Day 30 |
| Example 2 | 00 | 9 | 8 | 7 | 6 | 8 | 6 | 0 |
| Example 6 | 00 | 2 | 3 | 7 | 4 | 8 | 5 | 4 |
| Example 12 | 00 | 7 | 1 | 4 | 0 | 3 | 8 | 3 |

Figure 3:
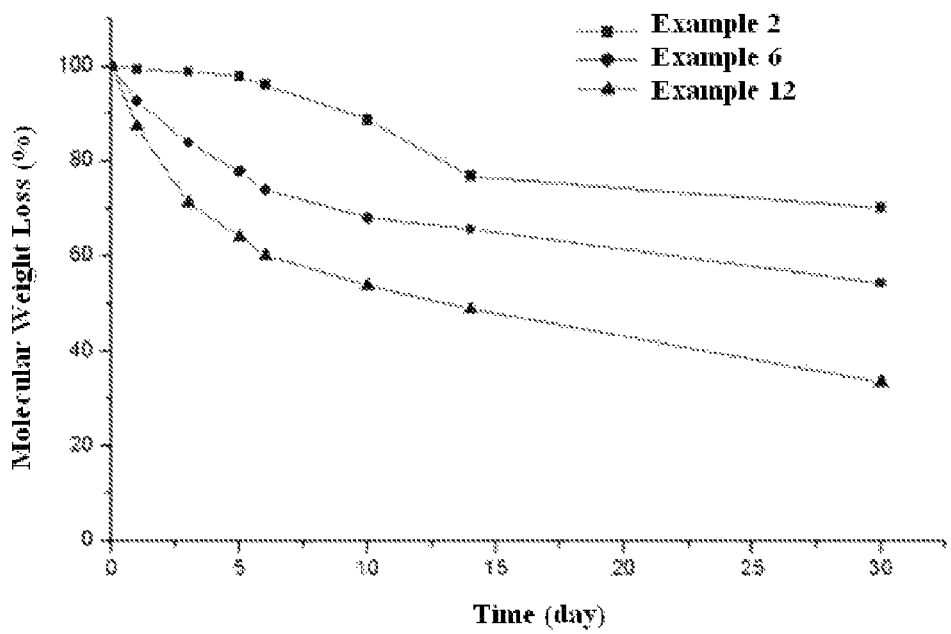
FIG. 3 shows the degree of hydrolysis of the thermosensitive poly(organophosphazene) with a functional group of the present invention with lapse of time.

The degree of hydrolysis of the poly(organophosphazene)s of the present invention with time is also shown in FIG. 3.

As known from Table 4 and FIG. 3, the poly(organophosphazene) with no carboxyl group according to Example 2 shows molecular weight reduction of about 5% after the initial 5 days, and about 30% after 30 days. The poly(organophosphazene) with a carboxyl group according to Example 6 shows the molecular weight reduction of about 23% after the initial 5 days, and about 46% after 30 days. Therefore, it is revealed that the poly(organophosphazene) with a carboxyl group shows a higher hydrolysis rate than that with no carboxyl group.

When the starting point of hydrolysis is an amino acid ester, the ester bond is cut off to generate a carboxyl group, and the generated carboxyl group attracts phosphorus atoms at the main chain or adjacent molecules to cut off the main chain. Therefore, the poly(organophosphazene) with a carboxyl group as a functional group shows relatively high hydrolysis rate, since it need not go through the step of cutting off the ester bond.

In the case of the poly(organophosphazene) with both of a carboxyl group and depsipeptide, which is known to accelerate the hydrolysis, according to Example 12, the molecular weight thereof is reduced by about 36% after the initial 5 days, continuously reduced thereafter, and reduced by about 67% after 30 days, showing the highest hydrolysis rate.

Example 16

Observation of the Sol-Gel Phase Transition with Temperature in the Mixture Comprising Various poly(organophosphazene)s Having Difference Properties in Various Mixture Ratios The poly(organophosphazene)s of Examples 7 and 8 have different properties from each other. That is, the polymer of Example 7 has the high gel solidity of 1058 Pa·s at the low gelling temperature of 27° C., whereas the polymer of Example 8 has the relatively low gel solidity of 65 Pa·s at the relatively high gelling temperature of 65° C. Such two polymers with the contrary properties to each other were mixed in various mixture ratios as shown in the following Table 5, and then, their sol-gel phase transition with temperature change was observed.

The obtained results of testing the gel properties in the mixture including the polymers of Examples 7 and 8 in various ratios depending on the temperature are shown in the following Table 5.

TABLE 5

| Mixture Ratio (%) | | Initial gelling temperature (° C.) | Maximum gelling temperature (° C.) | Maximum gel solidity (Pa · s) |
|---|---|---|---|---|
| Polymer of Example 7 | Polymer of Example 8 | | | |
| 0 | 100 | 36 | 51 | 65 |
| 40 | 60 | 27 | 41 | 148 |
| 46 | 54 | 25 | 40 | 253 |
| 52 | 48 | 23 | 39 | 310 |
| 100 | 0 | 18 | 27 | 1058 |

As shown from Table 5, as the content of the polymer of Example 8 having low maximum gel solidity and high maximum gelling temperature is lower, the mixture of the polymers has a higher maximum gel solidity and a lower maximum gelling temperature. Based on the results, it is possible to provide the mixture of the poly(organophosphazene)s having the desired maximum gel solidity and maximum gelling temperature by controlling the mixture ratio of the poly(organophosphazene)s having different properties.

Example 17

Observation of the Sol-Gel Phase Transition with Temperature in the Poly(Organophosphazene) with Chitosan In the present invention, when applied for a delivery material for injection type drugs, the poly(organophosphazene)s may further include various additives as occasion demands.

As an exemplary additive, chitosan may be employed due to its ability to ionically bind with drugs. The gel properties of the mixture including the poly(organophosphazene) of Example 3 and chitosan in various mixture ratios depending on the temperature are shown in the following Table 6.

TABLE 6

| Contents of Chitosan | Initial gelling temperature (° C.) | Maximum gelling temperature (° C.) | Maximum gel solidity (Pa · s) |
| --- | --- | --- | --- |
| 0 (v/w) % | 23 | 42 | 115 |
| 0.1 (v/w) % | 20 | 39 | 142 |
| 0.5 (v/w) % | 18 | 37 | 1013 |

As shown in Table 6, the maximum gelling temperature and the maximum gel solidity vary depending on the content of chitosan in the mixture. Based on the results, it is possible to provide the mixture containing the poly(organophosphazene)s having the desired maximum gel solidity and maximum gelling temperature suitable for the use as a delivery material for injection type drugs by controlling the kind and the content of the additives used.

Example 18

Solubility of Paclitaxel in the poly(organophosphazene) Solution

Paclitaxel which is an exemplary hydrophobic drug has been known to be insoluble in water. Only 0.004 mg of paclitaxel can be dissolved in 1 ml of water at 25° C. However, the present invention found that the solubility of the hydrophobic drugs such as paclitaxel can be considerably increased in the poly(organophosphazene) solution of the present invention.

The poly(organophosphazene) phosphate molecule of Example 3 is dissolved in buffered saline (pH 7.4), to make the poly(organophosphazene) phosphate with the concentration of 7 wt % and 10 wt %, respectively. An excess amount of paclitaxel was added and a dissolution reaction was performed in a chamber at 4° C. for three (3) days. Then, the non-dissolved paclitaxel was removed, and the amount of remaining paclitaxel was measured through HPLC.

The obtained results of the solubility of paclitaxel in the poly(organophosphazene) solution with various concentrations were shown in the following Table 7.

TABLE 7

| Solvent | Solubility (mg/ml) |
| --- | --- |
| Phosphate buffered saline | 0.0003 |
| Poly(organophosphazene) solution of 7 wt % | 4 |
| Poly(organophosphazene) solution of 10 wt % | 9 |

As shown in Table 7, the poly(organophosphazene) solutions have increased solubilities of 13,000 to 30,000 times more compared to phosphate buffered saline with no polymer. Further, the higher the concentration of the poly(organophosphazene) solution, the more the solubility increases.

Example 19

Observation of In Vitro Release Behavior of Paclitaxel in the poly(organophosphazene) Hydrogel The poly(organophosphazene) of Example 3 was dissolved in phosphate buffered saline to make a solution with the concentration of 7 wt %. 0.1 vol % of paclitaxel was dissolved in the obtained solution. The solution containing 0.5 ml of paclitaxel was put into a millicell at 37° C. to form a hydrogel.

The obtained poly(organophosphazene) hydrogel containing paclitaxel was added to 100 ml of a release solution. As the release solution, phosphate buffered saline (pH 7.4) containing 0.1 vol % of SDS was used.

Figure 4:
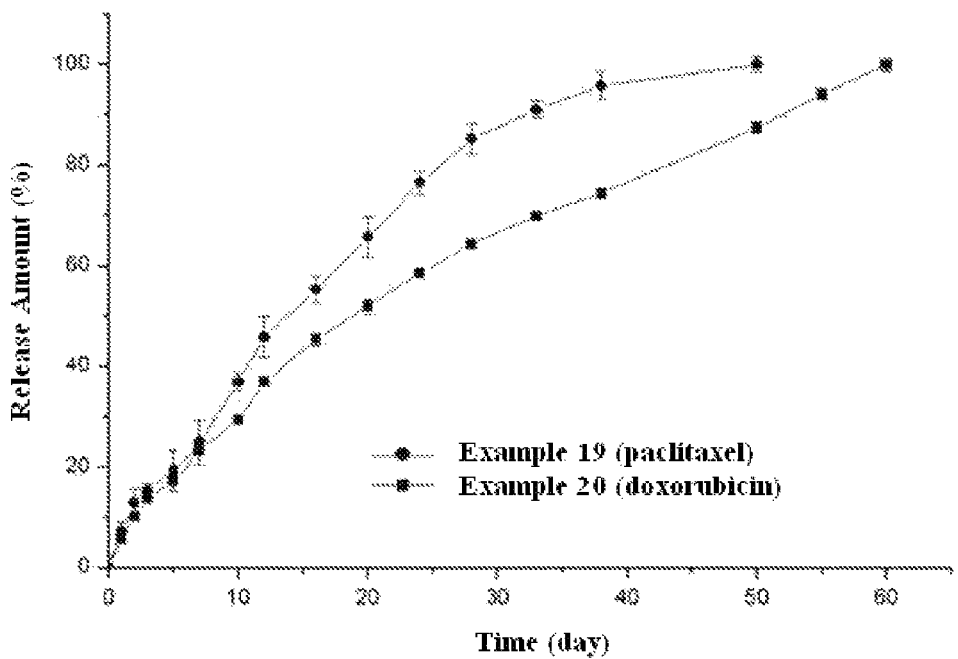
FIG. 4 shows the release behavior of anti-cancer drugs from the poly(organophosphazene) hydrogel with a functional group of the present invention with lapse of time.

The obtained release solution containing the paclitaxel-containing poly(organophosphazene) hydrogel was put into a bath at 37° C., and stirred at 50 rpm. Five (5) ml of the release solution was corrected at regular time intervals as shown in FIG. 4, and the released amount of paclitaxel was measured by HPLC. After correcting 5 ml of the release solution, an equal amount of fresh release solution was supplemented.

The release behavior of paclitaxel in the poly(organophosphazene) hydrogel with time is shown in FIG. 4. As shown in FIG. 4, the release of paclitaxel in the paclitaxel-containing poly(organophosphazene) hydrogel is well controlled and sustained, and the paclitaxel can be released for at least 50 days.

Example 20

Observation of In Vitro Release Behavior of Doxorubicin in the poly(organophosphazene) Hydrogel The poly(organophosphazene) of Example 4 was dissolved in water to make a solution with the concentration of 10 wt %. 0.1 vol % of doxorubicin was dissolved in the obtained solution. The solution containing 0.5 ml of doxorubicin was put into a millicell at 37° C. to form a hydrogel.

The obtained poly(organophosphazene) hydrogel containing doxorubicin was added to 10 ml of phosphate buffered saline (pH 7.4) used as a release solution. The obtained release solution containing the doxorubicin-containing poly(organophosphazene) hydrogel was put into a bath at 37° C. and stirred at 50 rpm. Then, the millicell was transferred into a fresh release solution. The released amount of doxorubicin in the release solution wherein the release of doxorubicin occurs was measured by using UV-VIS spectroscopy (excitation: 495 nm).

The release behavior of doxorubicin in the poly(organophosphazene) hydrogel with time is shown in FIG. 4. As shown in FIG. 4, the release of doxorubicin in the doxorubicin-containing poly(organophosphazene) hydrogel is well controlled and sustained, and the doxorubicin can be released for at least 60 days.

Example 21

Observation of In Vitro Release Behavior of Erythropoietin (EPO) in the poly(organophosphazene) Hydrogel The poly(organophosphazene) of Example 3 was dissolved in phosphate buffered saline to make a solution with the concentration of 12 wt %. 0.06 vol % of human erythropoietin (BioSource™, Invitrogen, US) was dissolved in the obtained solution. The solution containing 0.3 ml of erythropoietin was put into a millicell at 37° C. to form a hydrogel.

Figure 5:
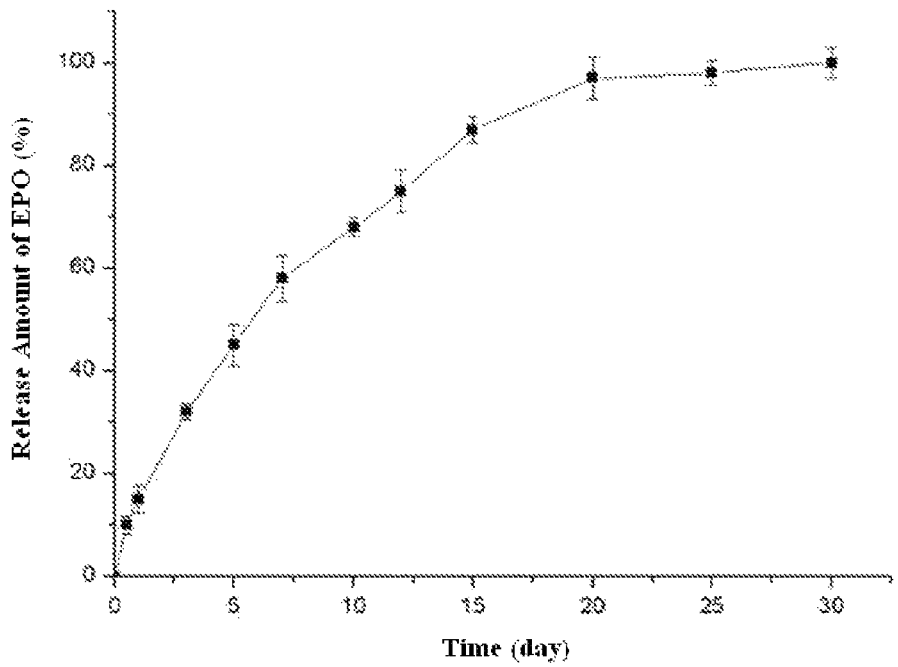
FIG. 5 shows the release behavior of erythropoietin from the poly(organophosphazene) hydrogel with a functional group of the present invention with lapse of time.

The obtained poly(organophosphazene) hydrogel containing erythropoietin was added to 10 ml of phosphate buffered saline (pH 7.4) used as a release solution. The obtained release solution containing the erythropoietin-containing poly(organophosphazene) hydrogel was put into a bath at 37° C. and stirred at 50 rpm. 0.5 ml of the release solution was corrected at regular time intervals as shown in FIG. 5, and the released amount of erythropoietin was measured by using erythropoietin immuno-assay and quantikine. After correcting 0.5 ml of the release solution, an equal amount of fresh release solution was supplemented.

The release behavior of erythropoietin in the poly(organophosphazene) hydrogel with time is shown in FIG. 5. As shown in FIG. 5, the release of erythropoietin in the erythropoietin-containing poly(organophosphazene) hydrogel is well controlled and sustained, whereby the paclitaxel can be released for at least 30 days.

Example 21

Observation of In Vitro Release Behavior of Human Growth Hormone (hGH) in the poly(organophosphazene) Hydrogel The poly(organophosphazene) of Example 3 was dissolved in phosphate buffered saline to make a solution with the concentration of 10 wt %. 0.5 vol % of human growth hormone (BioSource™, Invitrogen, US) was dissolved in the obtained solution. The solution containing 0.3 ml of human growth hormone was put into a millicell at 37° C. to form a hydrogel.

Figure 6:
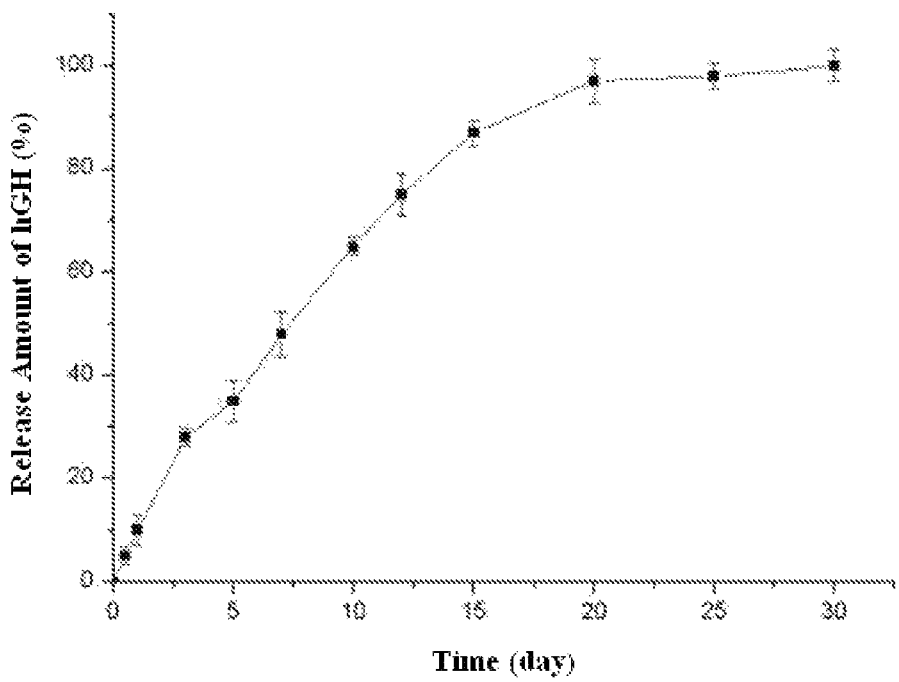
FIG. 6 shows the release behavior of the human growth hormone (hGH) from the poly(organophosphazene) hydrogel with a functional group of the present invention with lapse of time.

The obtained poly(organophosphazene) hydrogel containing human growth hormone was added to 10 ml of phosphate buffered saline (pH 7.4) used as a release solution. The obtained release solution containing the human growth hormone-containing poly(organophosphazene) hydrogel was put into a bath at 37° C. and stirred at 50 rpm. 0.5 ml of the release solution was corrected at regular time intervals as shown in FIG. 6, and the released amount of human growth hormone was measured by using human growth hormone immuno-assay and quantikine. After correcting 0.5 ml of the release solution, an equal amount of the fresh release solution was supplemented.

The release behavior of human growth hormone in the poly(organophosphazene) hydrogel with time is shown in FIG. 6. As shown in FIG. 6, the release of human growth hormone in the human growth hormone-containing poly (organophosphazene) hydrogel is well controlled and sustained, whereby the paclitaxel can be released for at least 30 days.

Example 23

Observation of Formation of Ionic Bond Between Additives and Protein Drugs

In the present invention, the additives that are capable of ionically binding with drugs to induce a controlled and sustained (slow) release of the drug, may be one or more selected form the following: cationic polymers such as poly-L-arginine, poly-L-lysine, poly(ethylene glycol), polyethyleneimine, chitosan, protamine, amiloride, procainamide, acetyl-beta-methylcholine, spermine, spermidine, and lysozyme; anionic polymers such as hyaluronic acid, chondroitin sulfate, heparin, and alginate; and the like.

In order to confirm the formation of an ion bond between the additives and drugs, gel electrophoresis was conducted. Poly-L-arginine with the molecular weight of 76600, polyethyleneimine with the molecular weight of 125000, and protamine with the molecular weight of 5100 were respectively used as the additives. Each of them was added to 0.01% albumin solution (Bovin Serum Albumin; BSA, Wako chemical) at various concentrations and sufficiently stirred. After holding for 20 minutes, an electrophoresis for each of the obtained solutions was conducted through polyacrylamide gel.

Figure 7:
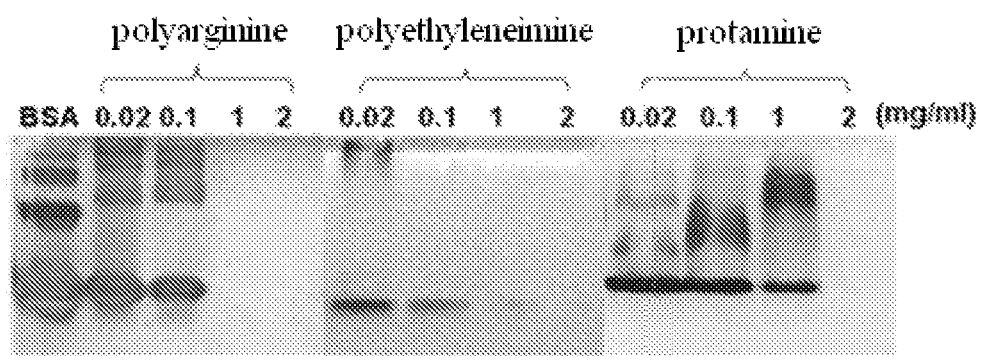
FIG. 7 shows that additives and protein drugs used in the present invention are ionically bound to the poly(organophosphazene) hydrogel with a functional group.

The results of the electrophoresis showing the formation of ionic bond between the additives and drugs are shown in FIG. 7. As shown in FIG. 7, the mixture of the additive (poly-L-arginine, polyethyleneimine, or protamine) and the protein drug (albumin) shows a worse development property of the gel as the concentration of the additive is higher. This result shows that as the additive's concentration is higher, the ionic bond between the additive and the drug is stronger.

Example 24

Observation of In Vitro Release Behavior of Gelatin in the poly(organophosphazene) Hydrogel with poly-L-arginine Poly(organophosphazene) of Example 3 was dissolved in phosphate buffered saline (pH 7.4) at the concentration of 10 wt %. Poly-L-arginine with the molecular weight of 76600 (Aldrich) was dissolved in the obtained solution at the concentration of 0.1 vol % and 1 vol %, respectively. Then, 0.1 vol % of gelatin (Aldrich) was dissolved in each solution. Poly-L-arginine/poly(organophosphazene) solution containing 0.5 ml of gelatin was put into a millicell to generate a hydrogel at 37° C. The obtained gelatin-containing poly-L-arginine/poly(organophosphazene) hydrogel was added to 10 ml of phosphate buffered saline (pH 7.4) used as a release solution. The obtained solution was put into a bath at 37° C., and stirred at 50 rpm. Then, the millicell was transferred to a fresh release solution. The released amount of gelatin was measured by bicinchoninic acid method (BCA assay) for the release solution to which gelatin is released.

Figure 8:
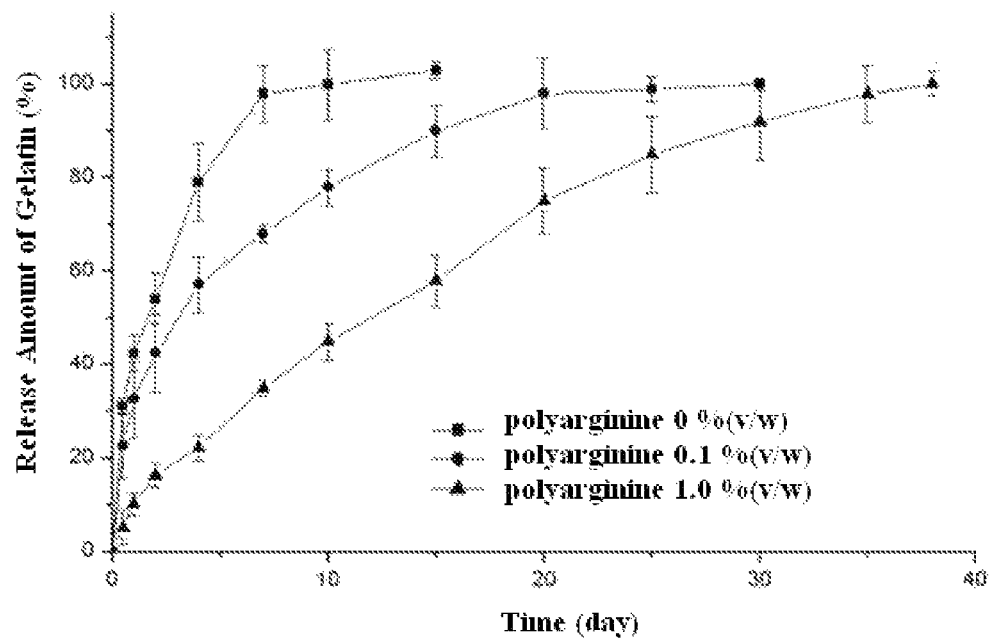
FIG. 8 shows the release behavior of gelatin from the poly(organophosphazene) hydrogel with polyarginine with lapse of time.

The release behavior of gelatin in the poly(organophosphazene) hydrogel containing poly-L-arginine at various concentrations is shown in FIG. 8. As shown in FIG. 8, gelatin is slowly released for about 7 days even in the poly-L-arginine-free poly(organophosphazene) hydrogel. Moreover, in the poly-L-arginine-containing poly(organophosphazene) hydrogel, the release of gelatin is sustained for at least 35 days due to the ionic bond between poly-L-arginine and gelatin. Further, it was observed that the more poly-L-arginine is contained, the more the ionic bonds are generated, resulting in a more sustained release of gelatin in the poly(organophosphazene) hydrogel.

Example 25

Observation of In Vitro Release Behavior of Albumin in the poly(organophosphazene) Hydrogel with Chitosan Poly(organophosphazene)s of Example 17 which contain chitosan at various concentrations were dissolved in water at the concentration of 10 wt %. Then, FITC-albumin (Aldrich) was dissolved in the obtained solution at the concentration of 0.1 vol %. Chitosan/poly(organophosphazene) solution containing 0.5 ml of FITC-albumin was put into a millicell to generate a hydrogel at 37° C. The obtained FITC-albumin-containing chitosan/poly(organophosphazene) hydrogel was added to 10 ml of phosphate buffered saline (pH 7.4) used as a release solution. The obtained solution was put into a bath at 37° C. and stirred at 50 rpm. Then, the millicell was transferred to a fresh release solution. The released amount of FITC-albumin was measured by using UV-VIS spectroscopy (excitation: 495 nm) for the release solution to which FITC-albumin is released.

Figure 9:
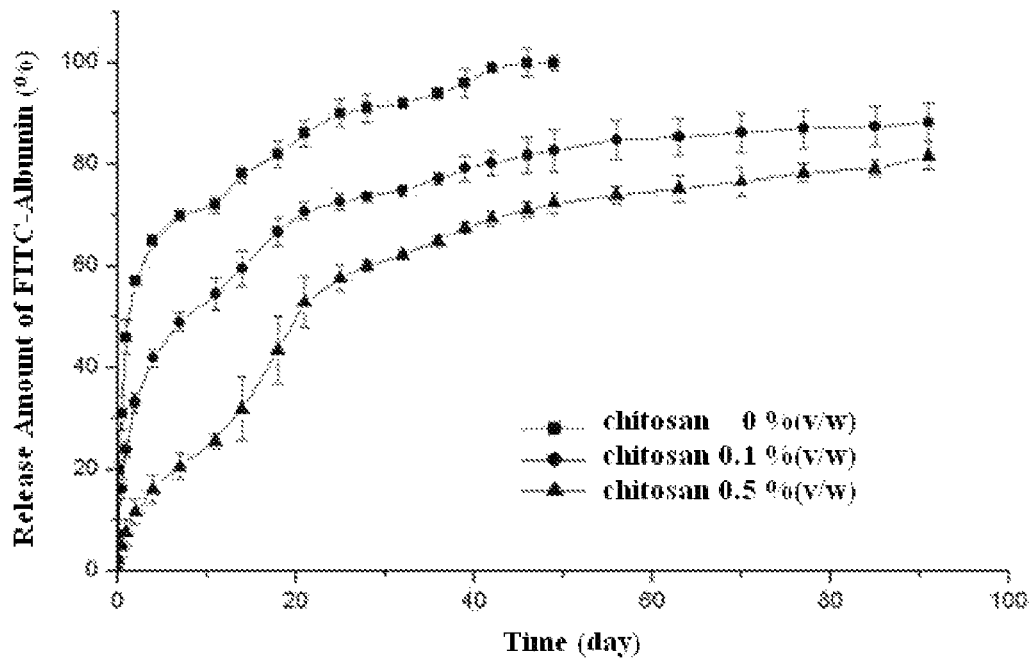
FIG. 9 shows the release behavior of FITC (fluorescein isothiocyanate)-albumin from the poly(organophosphazene) hydrogel with chitosan with lapse of time.

The release behavior of FITC-albumin in the poly(organophosphazene) hydrogel containing chitosan at various concentrations is shown in FIG. 9. As shown in FIG. 9, FITC-albumin is slowly released for about 40 days even in the chitosan-free poly(organophosphazene) hydrogel. Moreover, in the chitosan-containing poly(organophosphazene) hydrogel, the release of FITC-albumin is sustained for at least 90 days, due to the ionic bond between chitosan and FITC-albumin. Further, it was observed that the more chitosan is contained, the more the ionic bonds are generated, resulting in a more sustained release of FITC-albumin in the poly(organophosphazene) hydrogel.

Example 26

Observation of In Vivo Anti-Cancer Activity In Vivo of the poly(organophosphazene) Hydrogel Containing Paclitaxel In vivo anti-cancer activity of the poly(organophosphazene) hydrogel containing paclitaxel prepared by the method of Example 19 was determined by the following method.

A nude mouse (OrientalBio, Balb/C, female of 5-weeks old, 20 g) was used as an animal model for animal experimentation for an in vivo test. Cells of stomach cancer, SNU-601 ($1\times10^7$ cells, 0.2 ml, Korean Cell Line Bank), were injected into the dorsum of the mouse. A polymer solution containing the 10 wt % poly(organophosphazene) solution of Example 3, together with paclitaxel in the concentration of 0.4 vol % and 0.6 vol %, respectively, was prepared. 0.2 ml of the solution was injected into the cancer cells, and the change in the size of the cells was measured.

The anti-cancer effect of the poly(organophosphazene) solution containing 0.4 vol % of paclitaxel was determined at the administered amount of the solution of 40 mg/kg of the weight of mouse, and the anti-cancer effect of the poly(organophosphazene) solution containing 0.6 vol % of paclitaxel was determined at the administered amount of the solution of 60 mg/kg of the weight of mouse. For controls, the change of the size of the cancer cell was determined in the mouse administered with paclitaxel at the amount of 60 mg/kg of the weight of mouse, and in the mouse administered with saline only. Each test was conducted for ten (10) mice for each of the control groups and the experimental groups.

Figure 10:
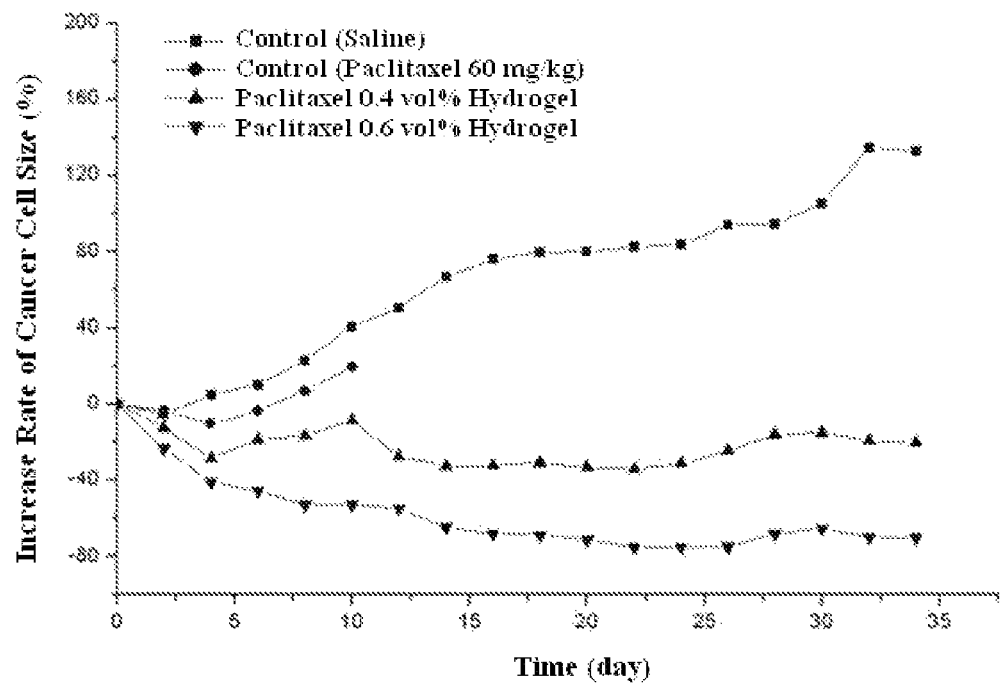
FIG. 10 shows in vivo anti-cancer activity of the poly(organophosphazene) containing paclitaxel.

The obtained results to the change of the size of the cancer cells in the control groups and the experimental groups administered with the poly(organophosphazene) solution containing paclitaxel are shown in FIG. 10.

As shown in FIG. 10, the control wherein only saline is administered to the cancer cell shows an increase in the cancer cell size by 83% at day 22 after administration, and by 134% at day 34 after administration. Whereas, the mice administered with the poly(organophosphazene) hydrogel containing 0.4 vol % of paclitaxel showed a decrease of 34% in the cancer cell at day 22 after administration, and maintained a decrease of 20% in the cancer cell at day 34 after administration. The mice administered with the poly(organophosphazene) hydrogel containing 0.6 vol % of paclitaxel showed a decrease of 75% in the cancer cell at day 22 after administration, and maintained a decrease of 70% in the cancer cell at day 34 after administration.

In the control administered with paclitaxel only at the concentration of 60 mg/kg, 8 mice died at day 10 after administration due to toxicity of paclitaxel. However, all the mice administered with the poly(organophosphazene) hydrogel containing 0.6 vol % of paclitaxel survived. Further, all the mice administered with the poly(organophosphazene) hydrogel containing 0.4 vol % of paclitaxel also survived.

Example 27

In Vivo Test for the poly(organophosphazene) Hydrogel Containing Therapeutic Cells and Additives The poly(organophosphazene) of Example 3 was dissolved in a cell culture solution (DMEM, Invitrogen) at the concentration of 10 wt %. To 200 μl of the obtained solution, rabbit cartilage cells ($10^6$ cells) (Samtako, using the primary cells established in a white rabbit of 2-weeks old), and 0.01 μl of 0.5 wt % transforming growth factor (TGF-beta) as an additive were added. 200 μl of the poly(organophosphazene) solution containing the cartilage cell ($10^6$ cell) and TGF-beta was subcutaneously injected into nude mice (OrientalBio, Balb/C, female of 5-weeks old, 20 g). The cell activity in the administered poly(organophosphazene) hydrogel was observed at weeks 4 and 7 after administration.

Figure 11:
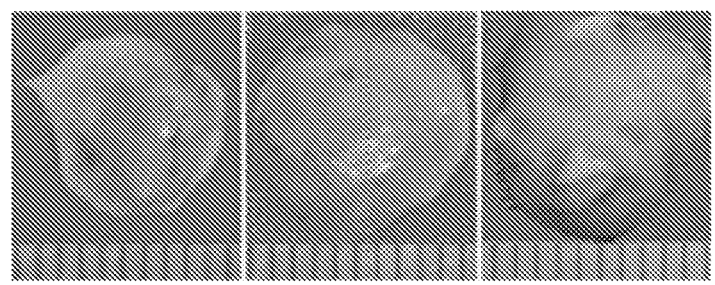
FIG. 11 shows in vivo activity of the poly(organophosphazene) hydrogel containing therapeutic cells.
Figure 11:
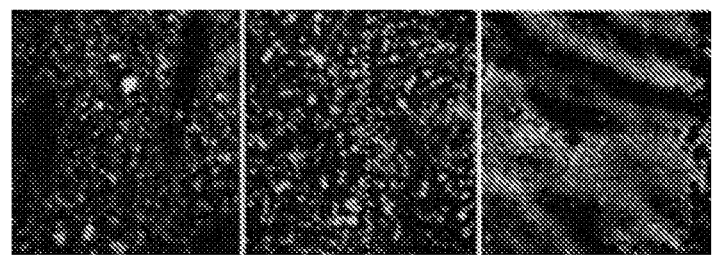

The increase of the cell activity in the poly(organophosphazene) hydrogel administered to the nude mice was determined by the change of the volume of the hydrogel and a tissue immuno-staining method (collagen 2). The results are shown in FIG. 11. As shown in FIG. 11, the cells in the hydrogel containing the therapeutic cells are increased with lapse of time in vivo, to cause the increase of the volume of the hydrogel. Furthermore, the results of the tissue immuno-staining show that the number of cells is also increased with time. Therefore, it can be confirmed that the cell activity is increased in the hydrogel of the present invention.

As aforementioned, the present invention provides poly (organophosphazene)s with functional groups capable of forming direct chemical bonds such as an ionic bond, showing the sol-gel phase transition depending on the temperature change and biodegradability in a living body. The poly(organophosphazene)s with functional groups can be used as a drug-delivery material capable of a sustained release for a long period due to the capability of forming direct chemical bonds. Furthermore, since the poly(organophosphazene)s with functional groups can directly bind with various polymers and bioactive substances, it is expected to be applied for various industrial fields relating to tissue engineering.

Further, the biodegradable thermosensitive poly(organophosphazene) hydrogel of the present invention used as a drug delivery material can increase the solubility of the drug and show sustained release behavior of the drug for at least 30 days as revealed through an in vitro test. In addition, the poly(organophosphazene) hydrogel containing additives for controlling the release rate show more sustained and controlled release of the drug due to the ionic bond between the additives and the drug, compared with the poly(organophosphazene) hydrogel with no additives.

Through in vivo drug activity tests, it is revealed that the poly(organophosphazene) hydrogel containing an anti-cancer drug according to the present invention can considerably inhibit the cancer cell growth when injected into a living body. Further, it is also observed that the poly(organophosphazene) hydrogel containing therapeutic cells and additives according to the present invention shows a good in vivo activity to effectively deliver the cells into a living body, and the delivered cells show normal cell growth.

In view of the above, the biodegradable and thermosensitive poly(organophosphazene) hydrogel containing a drug or therapeutic cells has advantages to be easily administered into a living body and shows good therapeutic effects due to the sustained release of a drug in vivo and/or in vitro or the improved activity of delivered cells.

What is claimed is:

1. A poly(organophosphazene) selected from the group consisting of:
   poly[(isoleucineethylester)$_{a1}$(isoleucineethylester)$_{a2}$(aminomethoxypolyethyleneglycol350)$_b$(glycine)$_d$phosphazene]$_n$,
   poly[(isoleucineethylester)$_{a1}$(isoleucineethylester)$_{a2}$(aminomethoxypolyethyleneglycol550)$_b$(glycylleucine)$_d$phosphazene]$_n$,
   poly[(isoleucineethylester)$_{a1}$(isoleucineethylester)$_{a2}$(aminomethoxypolyethyleneglycol550)$_b$(glycine)$_d$phosphazene]$_n$,
   poly[(isoleucineethylester)$_{a1}$(isoleucineethylester)$_{a2}$(ethyl-2-(O-glycyl)lactate)$_c$(aminomethoxypolyethyleneglycol750)$_b$(glycylglycine)$_d$phosphazene]$_n$, and
   poly[isoleucineethylester)$_{a1}$(isoleucineethylester)$_{a2}$(aminomethoxypolyethyleneglycol550)$_b$(glycylglycine)$_d$(glycylglycylpolyethyleneimine)$_e$phosphazene]$_n$,
   wherein a1, a2, b, c, d, and e respectively represent the content of each substituent, a1, a2, b, and d are independently selected from 0.01 to 1.9, c and e are independently from 0 to 1.9, and a1+a2+b+c+d+e=2.0, and n is from 5 to 100000.

2. A poly(organophosphazene) hydrogel containing the poly(organophosphazene) of claim 1 dissolved in one or more solvents and showing sol-gel phase transition depending on temperature change.

3. The hydrogel according to claim 2, wherein the solvent is one or more selected from the group consisting of water, buffer solution, acid solution, basic solution, salt solution, saline solution, water for injection, and glucose salt solution, and the concentration of the poly(organophosphazene) is from 1 to 50 wt %.

4. A bioactive substance delivery composition containing one or more poly(organophosphazene)s according to claim 1.

5. The bioactive substance delivery composition according to claim 4, wherein the bioactive substance is a drug selected from the group consisting of proteins, polypeptides, peptides, vaccines, genes, hormones, anti-cancer drugs, and angiogenesis inhibitors.

6. The bioactive substance delivery composition according to claim 4, further comprising one or more additives in the amount of $1\times10^{-6}$ to 30 wt %.

7. The bioactive substance delivery composition according to claim 6, wherein the additive is one or more selected from the group consisting of cationic polymers having the molecular weight from 200 to 750,000, poly(N-vinyl-2-pyrrolidone), polyvinylacetate (PVA), hyaluronic acid, chondroitin sulfate, heparin, alginate, amiloride, procainamide, acetyl-beta-methylcholine, spermine, spermidine, lysozyme, fibroin, albumin, collagen, growth factors, bone morphogenetic proteins (BMPs), dexamethason, fibronectin, fibrinogen, thrombin, proteins, cremophor EL, dexrazoxane, leucovorin, ricinoleic acid, phospholipid, small intestinal submucosa, vitamin E, polyglycerol ester of fatty acid, Labrafil, Labrafil M1944CS, citric acid, glutamic acid, hydroxypropyl methylcellulose, gelatin, isopropyl myristate, Eudragit, tego betain, dimyristoylphosphatidylcholine, scleroglucan, ethanol, dimethyl sulfoxide, preservatives, sugars, polyols, sugar-containing polyols, amino acids, polymer-containing polyols, sugar-containing amino acids, surfactants, sugar-containing ions, silicate, NaCl, KCl, NaBr, NaI, LiCl, n-Bu$_4$NBr, n-Pr$_4$NBr, Et$_4$NBr, Mg(OH)$_2$, Ca(OH)$_2$, ZnCO$_3$, Ca$_3$(PO$_4$)$_2$, ZnCl$_2$, (C$_2$H3O$_2$)$_2$Zn, ZnCO$_3$, CdCl$_2$, HgCl$_2$, CoCl$_2$, (CaNO$_3$)$_2$, BaCl$_2$, MgCl$_2$, PbCl$_2$, AlCl$_3$, FeCl$_2$, FeCl$_3$, NiCl$_2$, AgCl, AuCl$_3$, CuCl$_2$, sodium tetradecyl sulfate, dodecyltrimethylammonium bromide, dodecyltrmethylammonium chloride, and tetradecyltrimethylammonium bromide.

8. A bioactive substance delivery system containing one or more bioactive substances and one or more poly(organophosphazene)s according to claim 1.

9. The bioactive substance delivery system according to claim 8, wherein the bioactive substance is one or more selected from the group consisting of drugs and therapeutic cells.

10. The bioactive substance delivery system according to claim 9, wherein the drug is selected from the group consisting of proteins, polypeptides, peptides, vaccines, genes, hormones, anti-cancer drugs, and angiogenesis inhibitors and the content of the drug is from $1\times10^{-8}$ to 50 vol %.

11. The bioactive substance delivery system according to claim 10, wherein the protein, polypeptide, or peptide is one or more selected from the group consisting of erythropoietin (EPO), interferon-alpha, interferon-beta, interferon-gamma, growth hormone (human, pig, cow, etc.), growth hormone releasing factor, nerve growth factor (NGF), granulocyte-colony stimulating factor (G-CSF), granulocyte macrophage-colony stimulating factor (GM-CSF), macrophage-colony stimulating factor (M-CSF), blood clotting factor, insulin, oxytocin, vasopressin, adrenocorticotropic hormone, epidermal growth factor, platelet-derived growth factor (PDGF), prolactin, luliberin, luteinizing hormone releasing hormone (LHRH), LHRH agonists, LHRH antagonists, somatostatin, glucagon, interleukin-2 (IL-2), interleukin-11 (IL-11), gastrin, tetragastrin, pentagastrin, urogastrone, secretin, calcitonin, enkephalins, endorphins, angiotensins, thyrotropin releasing hormone (TRH), tumor necrosis factor (TNF), tumor necrosis factor related apoptosis inducing ligand (TRAIL), heparinase, bone morphogenic protein (BMP), human atrial natriuretic peptide (hANP), glucagon-like peptide (GLP-1), renin, bradykinin, bacitracins, polymyxins, colistins, tyrocidine, gramicidins, cyclosporins and synthetic analogs thereof, monoclonal antibody, antibody, a substance which is modified or shows the same effect of a drug, ferment, and cytokines;
   the vaccine is one or more selected from the group consisting of hepatitis vaccine;
   the gene is one or more selected from the group consisting of small interference RNA (siRNA), plasmid DNA, and antisense oligodeoxynucleotide (AS-ODN);
   the hormone is one or more selected from the group consisting of testosterone, estradiol, progesterone, prostaglandins and synthetic analogs thereof, and a substance which is modified or shows the same effect of a drug;
   the anti-cancer drug is one or more selected from the group consisting of paclitaxel, doxorubicin, 5-fluorouracil, cisplatin, carboplatin, oxaliplatin, tegafur, irinotecan, docetaxel, cyclophosphamide, cemcitabine, ifosfamide, mitomycin C, vincristine, etoposide, methotrexate, topotecan, tamoxifen, vinorelbine, camptothecin, danuorubicin, chlorambucil, bryostatin- 1, calicheamicin, mayatansine, levamisole, DNA recombinant interferon alfa-2a, mitoxantrone, nimustine, interferon alfa-2a, doxifluridine, formestane, leuprolide acetate, megestrol acetate, carmofur, teniposide, bleomycin, carmustine, heptaplatin, exemestane, anastrozole, estramustine, capecitabine, goserelin acetate, polysaccharide potassium, medroxypogesterone acetate, epirubicin, letrozole, pirarubicin, topotecan, altretamine, toremifene citrate, BCNU, taxotere, actinomycin D, polyethylene glycol conjugated protein, and synthetic analogs thereof, and a substance which is modified or shows the same effect of a drug; and the angiogenesis inhibitor is one or more selected from the group consisting of BMS-275291, Clodronate, 6-deoxy-6-demethyl-4-dedimethylaminotetracycline, Doxycycline, Marimastat, 2-Methoxyestradiol, Squalamine, SU5164, Thalidomide, TNP-470, Combretastatin A4, Soy Isoflavone, Enzastaurin, CC 5013, Celecoxib, ZD 6474, Halofuginone hydrobromide, interferon-alpha, Bevacizumab, AE-941, Interleukin-12, VEFG-trap, Cetuximab, and synthetic analogs thereof, and a substance which is modified or shows the same effect of a drug.

12. The bioactive substance delivery system according to claim 9, wherein the therapeutic cell is one or more selected from the group consisting of preosteoblast, chondrocyte, umbilical vein endothelial cell (UVEC), osteoblast, adult stem cell, schwann cell, oligodendrocyte, hepatocyte, mural cell (used in combination with UVEC), myoblast, insulin-secreting cell, endothelial cell, smooth muscle cell, fibroblast, β-cell, endodermal cell, hepatic stem cell, juxraglomerular cell, skeletal muscle cell, keratinocyte, melanocyte, langerhans cell, merkel cell, dermal fibroblast, and preadipocyte.

13. The bioactive substance delivery system according to claim 8, further comprising one or more additives in the amount of $1\times10^{-6}$ to 30 wt % based on the total weight.

14. The bioactive substance delivery system according to claim 13, wherein the additive is one or more selected from the group consisting of cationic polymers having the molecular weight from 200 to 750,000, poly(N-vinyl-2-pyrrolidone), polyvinylacetate (PVA), hyaluronic acid, chondroitin sulfate, heparin, alginate, amiloride, procainamide, acetyl-beta-methylcholine, spermine, spermidine, lysozyme, fibroin, albumin, collagen, growth factors, bone morphogenetic proteins (BMPs), dexamethason, fibronectin, fibrinogen, thrombin, proteins, cremophor EL, dexrazoxane, leucovorin, ricinoleic acid, phospholipid, small intestinal submucosa, vitamin E, polyglycerol ester of fatty acid, Labrafil, Labrafil M1944CS, citric acid, glutamic acid, hydroxypropyl methylcellulose, gelatin, isopropyl myristate, Eudragit, tego betain, dimyristoylphosphatidylcholine, scleroglucan, ethanol, dimethyl sulfoxide, preservatives, sugars, polyols, sugar-containing polyols, amino acids, polymer-containing polyols, sugar-containing amino acids, surfactants, sugar-containing ions, silicate, NaCl, KCl, NaBr, NaI, LiCl, n-Bu$_4$NBr, n-Pr$_4$NBr, Et$_4$NBr, Mg(OH)$_2$, Ca(OH)$_2$, ZnCO$_3$, Ca$_3$(PO$_4$)$_2$, ZnCl$_2$, (C$_2$H3O$_2$)$_2$Zn, ZnCO$_3$, CdCl$_2$, HgCl$_2$, CoCl$_2$, (CaNO$_3$)$_2$, BaCl$_2$, MgCl$_2$, PbCl$_2$, AlCl$_3$, FeCl$_2$, FeCl$_3$, NiCl$_2$, AgCl, AuCl$_3$, CuCl$_2$, sodium tetradecyl sulfate, dodecyltrimethylammonium bromide, dodecyltrmethylammonium chloride, and tetradecyltrimethylammonium bromide.

15. The bioactive substance delivery system according to claim 8, wherein an administration route for delivery is selected from the group consisting of oral administration, buccal administration, mucosal administration, nasal administration, intraperitoneal administration, hypodermic injection, muscular injection, percutaneous administration, and intratumoral administration.

16. A bioactive substance delivery composition containing one or more poly(organophosphazene) hydrogels according to claim 2.

17. The bioactive substance delivery composition according to claim 16, wherein the bioactive substance is a drug selected from the group consisting of proteins, polypeptides, peptides, vaccines, genes, hormones, anti-cancer drugs, and angiogenesis inhibitors.

18. The bioactive substance delivery composition according to claim 16, further comprising one or more additives in the amount of $1\times10^{-6}$ to 30 wt %.

19. The bioactive substance delivery composition according to claim 18, wherein the additive is one or more selected from the group consisting of cationic polymers having the molecular weight from 200 to 750,000, poly(N-vinyl-2-pyrrolidone), polyvinylacetate (PVA), hyaluronic acid, chondroitin sulfate, heparin, alginate, amiloride, procainamide, acetyl-beta-methylcholine, spermine, spermidine, lysozyme, fibroin, albumin, collagen, growth factors, bone morphogenetic proteins (BMPs), dexamethason, fibronectin, fibrinogen, thrombin, proteins, cremophor EL, dexrazoxane, leucovorin, ricinoleic acid, phospholipid, small intestinal submucosa, vitamin E, polyglycerol ester of fatty acid, Labrafil, Labrafil M1944CS, citric acid, glutamic acid, hydroxypropyl methylcellulose, gelatin, isopropyl myristate, Eudragit, tego betain, dimyristoylphosphatidylcholine, scleroglucan, ethanol, dimethyl sulfoxide, preservatives, sugars, polyols, sugar-containing polyols, amino acids, polymer-containing polyols, sugar-containing amino acids, surfactants, sugar-containing ions, silicate, NaCl, KCl, NaBr, NaI, LiCl, n-Bu$_4$NBr, n-Pr$_4$NBr, Et$_4$NBr, Mg(OH)$_2$, Ca(OH)$_2$, ZnCO$_3$, Ca$_3$(PO$_4$)$_2$, ZnCl$_2$, (C$_2$H3O$_2$)$_2$Zn, ZnCO$_3$, CdCl$_2$, HgCl$_2$, CoCl$_2$, (CaNO$_3$)$_2$, BaCl$_2$, MgCl$_2$, PbCl$_2$, AlCl$_3$, FeCl$_2$, FeCl$_3$, NiCl$_2$, AgCl, AuCl$_3$, CuCl$_2$, sodium tetradecyl sulfate, dodecyltrimethylammonium bromide, dodecyltrmethylammonium chloride, and tetradecyltrimethylammonium bromide.

20. A bioactive substance delivery system containing one or more bioactive substances and one or more poly(organophosphazene) hydrogels according to claim 2.

21. The bioactive substance delivery system according to claim 20, wherein the bioactive substance is one or more selected from the group consisting of drugs and therapeutic cells.

22. The bioactive substance delivery system according to claim 21, wherein the drug is selected from the group consisting of proteins, polypeptides, peptides, vaccines, genes, hormones, anti-cancer drugs, and angiogenesis inhibitors and the content of the drug is from $1\times10^{-8}$ to 50 vol %.

23. The bioactive substance delivery system according to claim 22, wherein the protein, polypeptide, or peptide is one or more selected from the group consisting of erythropoietin (EPO), interferon-alpha, interferon-beta, interferon-gamma, growth hormone (human, pig, cow), growth hormone releasing factor, nerve growth factor (NGF), granulocyte-colony stimulating factor (G-CSF), granulocyte macrophage-colony stimulating factor (GM-CSF), macrophage-colony stimulating factor (M-CSF), blood clotting factor, insulin, oxytocin, vasopressin, adrenocorticotropic hormone, epidermal growth factor, platelet-derived growth factor (PDGF), prolactin, luliberin, luteinizing hormone releasing hormone (LHRH), LHRH agonists, LHRH antagonists, somatostatin, glucagon, interleukin-2 (IL-2), interleukin-11 (IL-11), gastrin, tetragastrin, pentagastrin, urogastrone, secretin, calcitonin, enkephalins, endorphins, angiotensins, thyrotropin releasing hormone (TRH), tumor necrosis factor (TNF), tumor necrosis factor related apoptosis inducing ligand (TRAIL), heparinase, bone morphogenic protein (BMP), human atrial natriuretic peptide (hANP), glucagon-like peptide (GLP-1), renin, bradykinin, bacitracins, polymyxins, colistins, tyrocidine, gramicidins, cyclosporins and synthetic analogs thereof, monoclonal antibody, antibody, a substance which is modified or shows the same effect of a drug, ferment, and cytokines;

the vaccine is one or more selected from the group consisting of hepatitis vaccine;

the gene is one or more selected from the group consisting of small interference RNA (siRNA), plasmid DNA, and antisense oligodeoxynucleotide (AS-ODN);

the hormone is one or more selected from the group consisting of testosterone, estradiol, progesterone, prostaglandins and synthetic analogs thereof, and a substance which is modified or shows the same effect of a drug;

the anti-cancer drug is one or more selected from the group consisting of paclitaxel, doxorubicin, 5-fluorouracil, cisplatin, carboplatin, oxaliplatin, tegafur, irinotecan, docetaxel, cyclophosphamide, cemcitabine, ifosfamide, mitomycin C, vincristine, etoposide, methotrexate, topotecan, tamoxifen, vinorelbine, camptothecin, danuorubicin, chlorambucil, bryostatin-1, calicheamicin, mayatansine, levamisole, DNA recombinant interferon alfa-2a, mitoxantrone, nimustine, interferon alfa-2a, doxifluridine, formestane, leuprolide acetate, megestrol acetate, carmofur, teniposide, bleomycin, carmustine, heptaplatin, exemestane, anastrozole, estramustine, capecitabine, goserelin acetate, polysaccharide potassium, medroxypogesterone acetate, epirubicin, letrozole, pirarubicin, topotecan, altretamine, toremifene citrate, BCNU, taxotere, actinomycin D, polyethylene glycol conjugated protein, and synthetic analogs thereof, and a substance which is modified or shows the same effect of a drug; and the angiogenesis inhibitor is one or more selected from the group consisting of BMS-275291, Clodronate, 6-deoxy-6-demethyl-4-dedimethylaminotetracycline, Doxycycline, Marimastat, 2-Methoxyestradiol, Squalamine, SU5164, Thalidomide, TNP-470, Combretastatin A4, Soy Isoflavone, Enzastaurin, CC 5013, Celecoxib, ZD 6474, Halofuginone hydrobromide, interferon-alpha, Bevacizumab, AE-941, Interleukin-12, VEFG-trap, Cetuximab, and synthetic analogs thereof, and a substance which is modified or shows the same effect of a drug.

24. The bioactive substance delivery system according to claim 21, wherein the therapeutic cell is one or more selected from the group consisting of preosteoblast, chondrocyte, umbilical vein endothelial cell (UVEC), osteoblast, adult stem cell, schwann cell, oligodendrocyte, hepatocyte, mural cell (used in combination with UVEC), myoblast, insulin-secreting cell, endothelial cell, smooth muscle cell, fibroblast, β-cell, endodermal cell, hepatic stem cell, juxraglomerular cell, skeletal muscle cell, keratinocyte, melanocyte, langerhans cell, merkel cell, dermal fibroblast, and preadipocyte.

25. The bioactive substance delivery system according to claim 20, further comprising one or more additives in the amount of $1\times10^{-6}$ to 30 wt % based on the total weight.

26. The bioactive substance delivery system according to claim 25, wherein the additive is one or more selected from the group consisting of cationic polymers having the molecular weight from 200 to 750,000, poly(N-vinyl-2-pyrrolidone), polyvinylacetate (PVA), hyaluronic acid, chondroitin sulfate, heparin, alginate, amiloride, procainamide, acetyl-beta-methylcholine, spermine, spermidine, lysozyme, fibroin, albumin, collagen, growth factors, bone morphogenetic proteins (BMPs), dexamethason, fibronectin, fibrinogen, thrombin, proteins, cremophor EL, dexrazoxane, leucovorin, ricinoleic acid, phospholipid, small intestinal submucosa, vitamin E, polyglycerol ester of fatty acid, Labrafil, Labrafil M1944CS, citric acid, glutamic acid, hydroxypropyl methylcellulose, gelatin, isopropyl myristate, Eudragit, tego betain, dimyristoylphosphatidylcholine, scleroglucan, ethanol, dimethyl sulfoxide, preservatives, sugars, polyols, sugar-containing polyols, amino acids, polymer-containing polyols, sugar-containing amino acids, surfactants, sugar-containing ions, silicate, NaCl, KCl, NaBr, NaI, LiCl, n-$Bu_4$NBr, n-$Pr_4$NBr, $Et_4$NBr, $Mg(OH)_2$, $Ca(OH)_2$, $ZnCO_3$, $Ca_3(PO_4)_2$, $ZnCl_2$, $(C_2H3O_2)_2$Zn, $ZnCO_3$, $CdCl_2$, $HgCl_2$, $CoCl_2$, $(CaNO_3)_2$, $BaCl_2$, $MgCl_2$, $PbCl_2$, $AlCl_3$, $FeCl_2$, $FeCl_3$, $NiCl_2$, AgCl, $AuCl_3$, $CuCl_2$, sodium tetradecyl sulfate, dodecyltrimethylammonium bromide, dodecyltrmethylammonium chloride, and tetradecyltrimethylammonium bromide.

27. The bioactive substance delivery system according to claim 20, wherein an administration route for delivery is selected from the group consisting of oral administration, buccal administration, mucosal administration, nasal administration, intraperitoneal administration, hypodermic injection, muscular injection, percutaneous administration, and intratumoral administration.

* * * * *